United States Patent
Jaworski

(10) Patent No.: US 10,765,654 B2
(45) Date of Patent: Sep. 8, 2020

(54) METHODS AND COMPOUNDS FOR TREATING CANCER

(75) Inventor: Diane M. Jaworski, Milton, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 0 days.

(21) Appl. No.: 14/233,301

(22) PCT Filed: Jul. 19, 2012

(86) PCT No.: PCT/US2012/047433
§ 371 (c)(1),
(2), (4) Date: Jan. 16, 2014

(87) PCT Pub. No.: WO2013/013061
PCT Pub. Date: Jan. 24, 2013

(65) Prior Publication Data
US 2014/0142152 A1    May 22, 2014

Related U.S. Application Data

(60) Provisional application No. 61/509,173, filed on Jul. 19, 2011.

(51) Int. Cl.
| | | |
|---|---|---|
| A61K 31/225 | (2006.01) |
| A61K 31/4188 | (2006.01) |
| A61K 31/22 | (2006.01) |
| A61K 31/475 | (2006.01) |
| A61K 31/166 | (2006.01) |
| A61K 31/175 | (2006.01) |
| A61K 45/06 | (2006.01) |

(52) U.S. Cl.
CPC .......... *A61K 31/225* (2013.01); *A61K 31/166* (2013.01); *A61K 31/175* (2013.01); *A61K 31/22* (2013.01); *A61K 31/4188* (2013.01); *A61K 31/475* (2013.01); *A61K 45/06* (2013.01)

(58) Field of Classification Search
None
See application file for complete search history.

(56) References Cited

U.S. PATENT DOCUMENTS

2007/0111979 A1    5/2007    Bishop
2013/0323300 A1*  12/2013    Olin et al. .................... 424/450

FOREIGN PATENT DOCUMENTS

WO    2013013061 A1    1/2013

OTHER PUBLICATIONS

Simone, Oncology: Introduction, Cecil Textbook of Medicine, 20th Edition, 1996 vol. 1, pp. 1004-1010.*
Hsu, Cancer Cell Metabolism: Warburg and Beyond, Cell, 2008, 134, pp. 703-707.*
PCT/US2012/047433, Nov. 2, 2012, International Search Report.
(Continued)

*Primary Examiner* — Savitha M Rao
*Assistant Examiner* — Andrew P Lee
(74) *Attorney, Agent, or Firm* — Pierce Atwood LLP

(57) ABSTRACT

The invention includes, in part, methods and compounds for treating cancer including, but not limited to gliomas, melanomas, and neuroblastomas. In some embodiments of the invention, a glyceryltriacetate compound is administered to a subject in an amount effective to treat or prevent a cancer in the subject.

11 Claims, 9 Drawing Sheets

(56) References Cited

OTHER PUBLICATIONS

PCT/US2012/047433, Nov. 2, 2012 Written Opinion of the International Searching Authority.
Adamson, C, et al., "Glioblastoma multiforme: a review of where we have been and where we are going", Expert Opin Investig Drugs, 2009, 18:1061-83.
Barker, P.B., et. al., "Quantitation of NAA in the Brain by Magnetic Resonance Spectroscopy" in "N-Acetylaspartate: A Unique Neuronal Molecule in the Central Nervous System", 2006, J.R. Moffett, et al., Editors. Springer: New York. 183-197.
Bhakoo, et al., "Developmental and regional distribution of aspartoacylase in rat brain tissue", (2001) Journal of Neurochemistry, 79:211-20.
Bhakoo, K.K., et al., "In vitro expression of N-acetyl aspartate by oligodendrocytes: implications for proton magnetic resonance spectroscopy signal in vivo.", Journal of Neurochemistry, 2000, 74:254-62.
Jung et al., "Lines of Murine Oligodendroglial Precursor Cells Immortalized by an Activated neuTyrosine Kinase Show Distinct Degrees of Interaction with Axons In Vitro and In Vivo", Jun. 1995, European Journal of Neuroscience, vol. 7, Issue 6, pp. 1245-1265.
Lluri et al., "Tissue Inhibitor of Metalloproteinase-2 (TIMP-2) regulates myogenesis and β1 integrin expression in vitro", Exp Cell Res, 2008, 314:11-24.
Long, PM, et al., "Differential Aminoacylase Expression in Neuroblastoma", Int J. Cancer, 2011, 129:1322-30.
Madhavarao et al., "Immunohistochemical Localization of Aspartoacylase in the Rat Central Nervous System", The Journal of Comparative Neurology, 2004, 472:318-29.
Madhavarao et al., "Glyceryl triacetate for Canavan disease: a low-dose trial in infants and evalution of a higer dose for toxicity in the tremor rat model", J Inherit Metab Dis (2009) 32:640-650.
Mathew, Raji et al., "Progress toward Acetate Supplementation Therapy for Canavan Disease: Glyceryl Triacetate Administration Increases Acetate, but Not N-Acetylaspartate, Levels in Brain", The Journal of Pharmacology and Experimental Therapeutics, 2005, vol. 315, No. 1, pp. 297-303.
Moffett, Jr, et. al., "N-Acetylaspartate in the CNS: From Neurodiagnostics to Neurobiology" (2007) Prog Neurobiol, 2007, 81:89-131.
Peethambaran Arun et al., "Metabolic acetate therapy improves phenotype in the tremor rat model of Canavan disease", Journal of Inherited Metabolic disease, vol. 33, No. 3, May 13, 2010, pp. 195-210.
Perez-Martinez, L. et al., "Tissue Inhibitor of Metalloproteinase-2 promotes neuronal differentiation by acting as an anti-mitogenic signal", J Neurosci, 2005, 25:4917-29.
Post & Dawson, "Characterization of a cell line derived from a human oligodendroglioma", Mol. Chem. Neuropathol., Jun. 1992, 16(3): 303-17.
Reitman, Z.J., et. al., "Profiling the effects of isocitrate dehydrogenase 1 and 2 mutations on the cellular metabolome", Proc Natl Acad Sci USA, 2011, 108:3270-5.
Sarkar, C. et al., "Loss of heterozygosity of a locus in the chromosomal region 17p13.3 is associated with increased cell proliferation in astrocytic tumors", Cancer Genet Cytogenet, Jul. 2003, 144(2):156-64.
Segel, Reeval et al., "A safety trial of high dose glyceryl triacetate for Canavan disease", Molecular Genetics and Metabolism, 2011, 203-206.
Swingler et al., "Degradome expression profiling in human articular cartilage", Arthritis Research & Therapy, Jun. 23, 2009, 11:R96.
Trissel, LA, et al., "Temozolomide Stability in Extemporaneously Compounded Oral Suspensions", Int J Pharm Compound, Sep.-Oct. 2006, 10(5): 396-399.
International Search Report and the Written Opinion of the International Searching Authority for Application No. PCT/US2012/047433 dated Nov. 2, 2012, 12 pages.
"Cytoxan—FDA Prescribing Information, Side Effects and Uses", Retreived from "http://www.drugs.com/pro/cytoxan.html" on Sep. 1, 2015, 17 pages.
"Merriam-Webster's Collegiate Dictionary, Eleventh Edition", Merriam-Webster, Incorporated, Springfield, MA, (2012), p. 430.
"FDA Approval for Gemcitabine Hydrochloride", National Cancer Institute, Retrieved from "http://www.cancergov/about-cancer/treatment/drugs/fda-gemcitabine-hydrochloride" on Sep. 1, 2015, 7 pages.
"FDA Approval for Sunitinib Malate", National Cancer Institute, Retrieved from "http://www.cancer.gov/about-cancer/treatment/drugs/fda-sunitinib-malate" on Sep. 1, 2015, 4 pages.
Semenza et al., "The Metabolism of Tumours': 70 Years Later", Novartis Found Symp. 2001;240:251-60; 2001. Abstract Only.
Scatena et al., "Revisiting the Warburg effect in cancer cells with proteomics. The emergence of new approaches to diagnosis, prognosis and therapy", Proteomics Clin Appl., Feb. 2010, vol. 4, pp. 143-158. Abstract Only.
Fraga, M.F. et al., "Loss of acetylation at Lys16 and trimethylation at Lys20 of histone H4 is a common hallmark of human cancer", Nature Genetics, Apr. 2005, vol. 37, pp. 391-400.
Glozak, M.A. and E. Seto, "Histone deacetylases and cancer", Oncogene, 2007, vol. 26, pp. 5420-5432.
Pfister, S. et al., "The histone acetyltransferase hMOF is frequently downregulated in primary breast carcinoma and medulloblastoma", International Journal of Cancer, Mar. 2007, pp. 1207-1213.
Qing et al., "Combinatorial Regulation of Neuroblastoma Tumor Progression by N-Myc and Hypoxia Inducible Factor HIF-1a." Cancer Research (2010), 70:10351-10361.

* cited by examiner

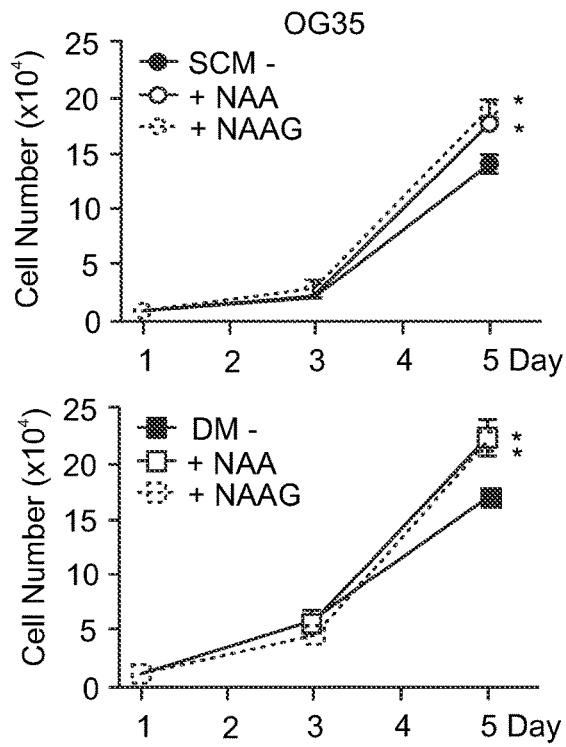
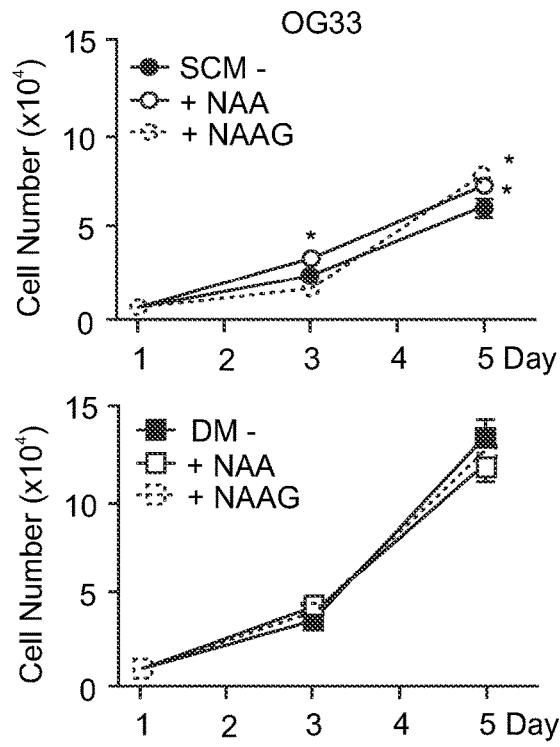
FIG. 4A
FIG. 4B
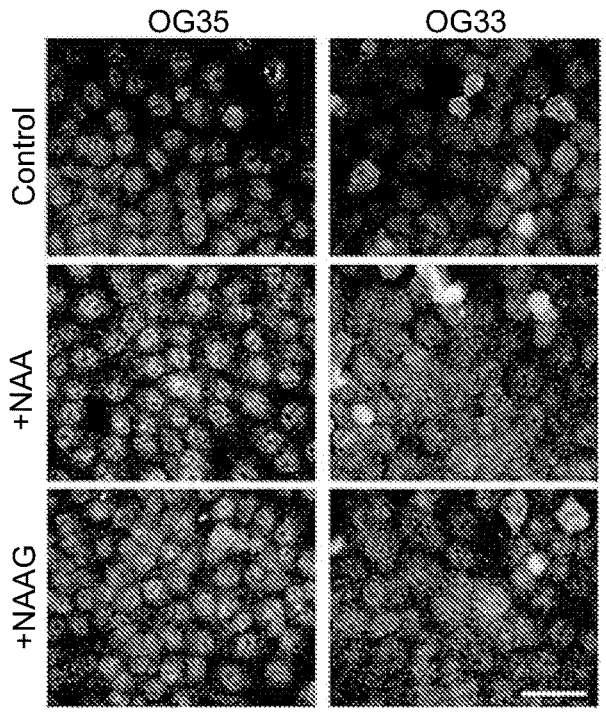
FIG. 4C

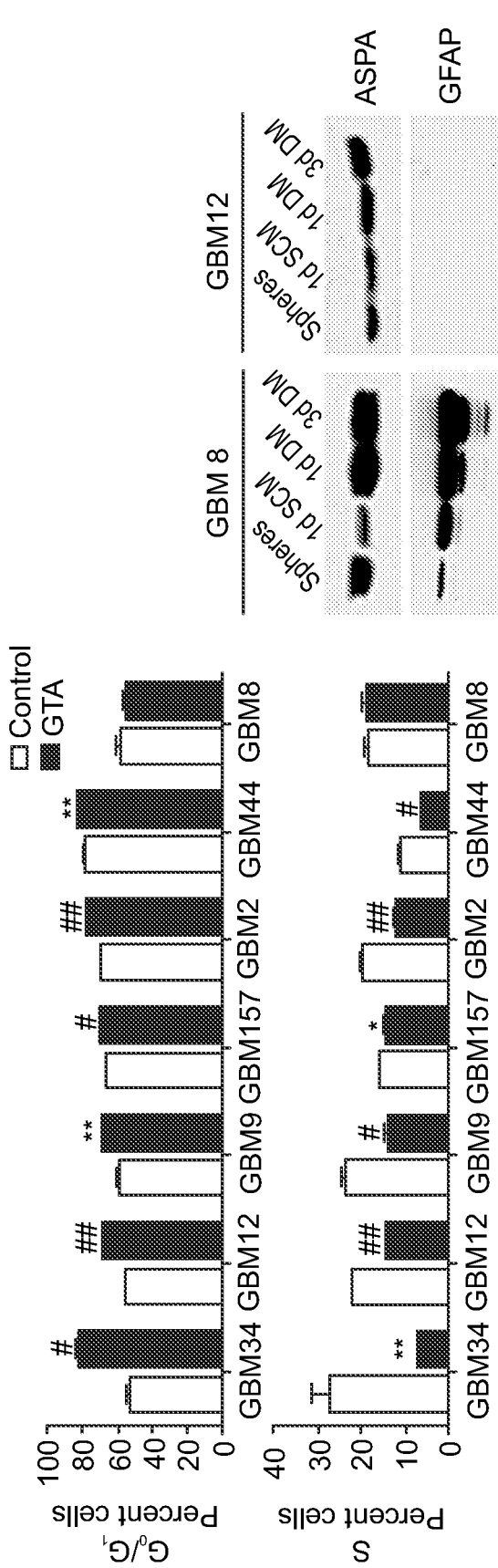
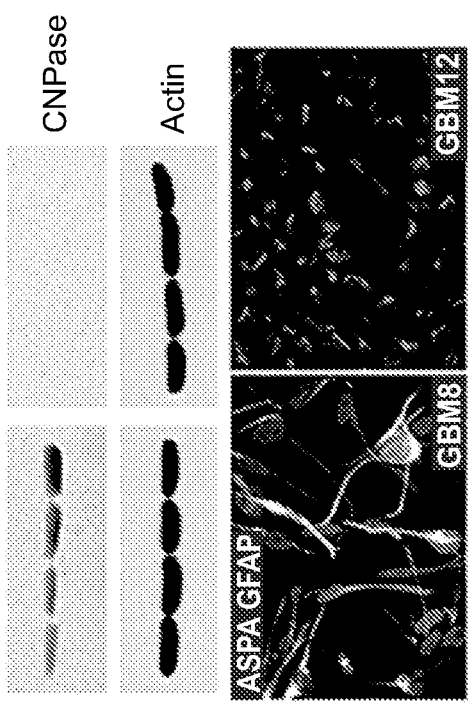
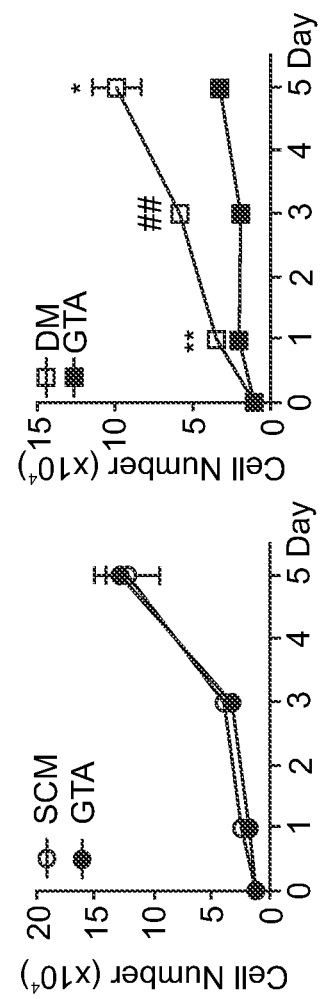
FIG.6A
FIG.6B
FIG.6C

METHODS AND COMPOUNDS FOR TREATING CANCER

RELATED APPLICATIONS

This application is a National Stage Filing under U.S.C. § 371 of PCT International Application PCT/US2012/47433, filed Jul. 19, 2012 which was published under PCT Article 21(2) in English, which claims benefit under 35 U.S.C. 119(e) of U.S. Provisional Application No. 61/509,173, filed Jul. 19, 2011, the entire content of each application is incorporated by reference herein.

GOVERNMENT INTEREST

This invention was made with government support under P20 RR016435 awarded by the National Institutes of Health. The Government has certain rights in the invention.

FIELD OF THE INVENTION

The invention relates, in part, to methods and compounds for treating cancer in a subject.

BACKGROUND

Despite multidisciplinary approaches, the median survival for patients with primary malignant brain tumors (i.e., glioma) is approximately one year. This prognosis has remained largely unchanged for decades. The ability to cure gliomas and other types of cancers is greatly hindered if at the time of diagnosis tumor cells have metastasized and have invaded distant sites, making surgical resection palliative rather than curative. Another treatment challenge for cancers is recurrence due to the persistence of chemotherapy-resistant and radiation-resistant cells, including in some cases, resistant glioma stem cells (GSCs).

SUMMARY OF THE INVENTION

According to one aspect of the invention, methods for treating a cancer are provided. The methods include administering to a subject in need of treatment of a cancer, a glyceryltriacetate (GTA) compound in a therapeutically effective amount to treat the cancer. In some embodiments, treating the cancer includes increasing cancer stem cell differentiation in the subject. In certain embodiments, the GTA compound is administered in an amount sufficient to increase cancer stem cell differentiation in the subject. In some embodiments, treating the cancer includes decreasing cancer stem cell proliferation in the subject. In some embodiments, the GTA compound is administered in an amount sufficient to decrease cancer stem cell proliferation in the subject. In some embodiments, treating the cancer includes enhancing the cytosolic-nuclear shuttling of aspartoacylase (ASPA) and/or acetyl-CoA synthetase 1 (AceCS1). In certain embodiments, the GTA compound is administered in an amount sufficient to enhancing the cytosolic-nuclear shuttling of aspartoacylase (ASPA) and/or acetyl-CoA synthetase 1 (AceCS1) in the subject. In some embodiments, the GTA compound is administered to the subject orally, intragastrically, or is administered into a surgical incision, opening, or cavity in the subject. In some embodiments, the treatment is a prophylactic treatment. In certain embodiments, the cancer is a glioma, a melanoma, or a neuroblastoma. In some embodiments, the cancer is a cancer in which aspartoacylase (ASPA) and/or N-acetylaspartate (NAA) expression and/or activity are decreased. In some embodiments, the method also includes administering one or more additional cancer-therapeutic agents to the subject. In some embodiments, the one or more additional cancer-therapeutic agents is temozolomide, bevacizumab, bis-chloroethylnitrosourea (BCNU), Lomustine, procarbazine, or vincristine. In certain embodiments, the GTA compound and the one or more additional cancer chemotherapeutic agent are administered as a combination drug therapy. In some embodiments, the treatment further includes a surgical treatment to remove or reduce the cancer in the subject. In some embodiments, one administration of the GTA compound to the subject includes between 0.01 and 15 grams of GTA per kg of the subject's body weight. In certain embodiments, one administration of the GTA compound to the subject includes at least 0.01, 0.05, 0.1, 0.5, 1, 2, 3, 4, 5, 6, 7, 8, 9, 10, 11, 12, 13, 14, or 15 grams of GTA per kg of the subject's body weight. In some embodiments, the dose is administered to the subject over a time period of up to 1, 5, 10, 15, 20, 30, 40, 50, 60, 120, 180, 240, 300, 360, 420, 480, 540, 600 minutes. In some embodiments, the total amount of GTA compound administered to the subject in a single day is between 0.1 and 100 g/kg body weight. In certain embodiments, the GTA compound is administered to the subject more than once and wherein the frequency of administration is at least once per month, once per week, every other day, or once per day. In some embodiments, the GTA compound is administered to the subject in a pharmaceutical composition. In some embodiments, the subject does not have Canavan disease. In some embodiments, the subject is a human. In certain embodiments, the subject is not undergoing treatment with the GTA compound for a non-cancer indication. In some embodiments, the subject is free of any indications otherwise calling for treatment with the GTA compound.

According to another aspect of the invention, articles of manufacture are provided. The articles of manufacture, also referred to as kits, include packaging material and a glyceryltriacetate (GTA) compound, wherein the article of manufacture also includes a label or package insert indicating that the GTA compound can be administered to a subject for treating or preventing a cancer. In some embodiments, the cancer is a glioma, a melanoma, or a neuroblastoma. In some embodiments, the cancer is a cancer in which aspartoacylase (ASPA) and/or N-acetylaspartate (NAA) expression and/or activity are decreased. In certain embodiments, the article of manufacture also includes one or more non-glyceryltriacetate chemotherapeutic agents to treat the cancer. In some embodiments, the non-glyceryltriacetate chemotherapeutic agent is temozolomide, bevacizumab, bis-chloroethylnitrosourea (BCNU), Lomustine, procarbazine, or vincristine.

According to another aspect of the invention, use of a glyceryltriacetate (GTA) compound in the manufacture of a medicament for the treatment of cancer is provided. In some embodiments, the cancer is a glioma, a melanoma, or a neuroblastoma. In some embodiments, the cancer is a cancer in which aspartoacylase (ASPA) and/or N-acetylaspartate (NAA) expression and/or activity are decreased. In certain embodiments, the treatment includes a prophylactic treatment.

According to yet another aspect of the invention, methods of administering a glyceryltriacetate (GTA) compound for the treatment of cancer are provided. In some embodiments, the GTA compound is administered to a subject in need of such treatment. In some embodiments, the subject does not have Canavan disease. In some embodiments, the subject is a human. In certain embodiments, the cancer is a glioma, a melanoma, or a neuroblastoma. In some embodiments, the cancer is a cancer in which aspartoacylase (ASPA) and/or N-acetylaspartate (NAA) expression and/or activity are decreased. In some embodiments, the subject is not undergoing treatment with the GTA compound for a non-cancer indication. In some embodiments, the subject is free of any indications otherwise calling for treatment with the GTA compound. In certain embodiments, one administration of the GTA compound to the subject includes between 0.01 and 15 grams of GTA per kg of the subject's body weight. In some embodiments, one administration of the GTA compound to the subject includes at least 0.01, 0.05, 0.1, 0.5, 1, 2, 3, 4, 5, 6, 7, 8, 9, 10, or 15 grams of GTA per kg of the subject's body weight. In some embodiments, the dose is administered to the subject over a time period of up to 1, 5, 10, 15, 20, 30, 40, 50, 60, 120, 180, 240, 300, 360, 420, 480, 540, 600 minutes. In some embodiments, the total amount of GTA compound administered to the subject in a single day is between 0.1 and 100 g/kg body weight. In some embodiments, the method also includes administering one or more non-glyceryltriacetate chemotherapeutic agents to treat the cancer. In certain embodiments, the non-glyceryltriacetate chemotherapeutic agent is temozolomide, bevacizumab, bis-chloroethylnitrosourea (BCNU), Lomustine, procarbazine, or vincristine. In some embodiments, the GTA compound is administered to the subject orally, intragastrically, or is administered into a surgical incision, opening, or cavity in the subject.

According to another aspect of the invention, methods for treating a cancer are provided. The methods include administering to a subject in need of treatment of a cancer a therapeutically effective amount of a compound that enhances the cytosolic-nuclear shuttling of aspartoacylase (ASPA) and/or acetyl-CoA synthetase 1 (AceCS1) in the subject. In some embodiments, the compound includes a glyceryltriacetate (GTA) compound. In certain embodiments, the GTA compound is administered orally, intragastrically, or is administered into a surgical opening, cavity, or incision in the subject. In some embodiments, the method also includes administering one or more non-glyceryltriacetate chemotherapeutic agents to treat the cancer. In some embodiments, the non-glyceryltriacetate chemotherapeutic agent is temozolomide, bevacizumab, bis-chloroethylnitrosourea (BCNU), Lomustine, procarbazine, or vincristine. In certain embodiments, the subject does not have Canavan disease. In some embodiments, the subject is a human. In some embodiments, the subject is not undergoing treatment with the GTA compound for a non-cancer indication. In some embodiments, the subject is free of any indications otherwise calling for treatment with the GTA compound. In certain embodiments, one administration of the GTA compound to the subject includes between 0.01 and 15 grams of GTA per kg of the subject's body weight. In some embodiments, one administration of the GTA compound to the subject includes at least 0.01, 0.05, 0.1, 0.5, 1, 2, 3, 4, 5, 6, 7, 8, 9, 10, or 15 grams of GTA per kg of the subject's body weight. In some embodiments, the dose is administered to the subject over a time period of up to 1, 5, 10, 15, 20, 30, 40, 50, 60, 120, 180, 240, 300, 360, 420, 480, 540, 600 minutes. In some embodiments, the total amount of GTA compound administered to the subject in a single day is between 0.1 and 100 g/kg body weight.

According to yet another aspect of the invention, a glyceryltriacetate (GTA) compound for use in treating a cancer is provided. In certain embodiments, the cancer is a glioma, a melanoma, or a neuroblastoma. In some embodiments, the cancer is a cancer in which aspartoacylase (ASPA) and/or N-acetylaspartate (NAA) expression and/or activity are decreased. In some embodiments, the treatment includes a prophylactic treatment. In certain embodiments, the GTA compound is co-administered with one or more non-glyceryltriacetate chemotherapeutic agents to treat the cancer. In some embodiments, the non-glyceryltriacetate chemotherapeutic agent is temozolomide, bevacizumab, bis-chloroethylnitrosourea (BCNU), Lomustine, procarbazine, or vincristine. In some embodiments, treating the cancer includes administering the GTA compound in a dosage range between 0.01 and 10 grams of GTA per kg (w/w). In certain embodiments, a single dose administration of the GTA compound includes at least 0.01, 0.05, 0.1, 0.5, 1, 2, 3, 4, 5, 6, 7, 8, 9, 10, 11, 12, 13, 14, or 15 grams of GTA per kg (w/w). In some embodiments, the dose is administered over a time period of up to 1, 5, 10, 15, 20, 30, 40, 50, 60, 120, 180, 240, 300, 360, 420, 480, 540, 600 minutes. In some embodiments, treating the cancer includes administering the GTA compound in a total dosage per day of between 0.1 and 100 g/kg body weight/day.

According to another aspect of the invention, pharmaceutically acceptable compositions that include an effective amount of a glyceryltriacetate (GTA) compound for use in treating cancer are provided. In some embodiments the cancer is a glioma, a melanoma, or a neuroblastoma. In certain embodiments, the cancer is a cancer in which aspartoacylase (ASPA) and/or N-acetylaspartate (NAA) expression and/or activity are decreased. In some embodiments, the treatment includes a prophylactic treatment. In some embodiments, the GTA compound is co-administered with one or more non-glyceryltriacetate chemotherapeutic agents to treat the cancer. In some embodiments, the non-glyceryltriacetate chemotherapeutic agent is temozolomide, bevacizumab, bis-chloroethylnitrosourea (BCNU), Lomustine, procarbazine, or vincristine. In certain embodiments, treating the cancer includes administering the GTA compound in a dosage range between 0.01 and 10 grams of GTA per kg (w/w). In some embodiments, a single dose administration of the GTA compound includes at least 0.01, 0.05, 0.1, 0.5, 1, 2, 3, 4, 5, 6, 7, 8, 9, 10, 11, 12, 13, 14, or 15 grams of GTA per kg (w/w). In certain embodiments, the dose is administered over a time period of up to 1, 5, 10, 15, 20, 30, 40, 50, 60, 120, 180, 240, 300, 360, 420, 480, 540, 600 minutes. In some embodiments, treating the cancer includes administering the GTA compound in a total dosage per day of between 0.1 and 100 g/kg body weight/day.

This invention is not limited in its application to the details of construction and the arrangement of components set forth in the following description or illustrated in the drawings. The invention is capable of other embodiments and of being practiced or of being carried out in various ways. The present invention is not intended to be limited to a system or method that must satisfy one or more of any stated objects or features of the invention. The present invention is not limited to the exemplary or primary embodiments described herein. Modifications and substitutions by one of ordinary skill in the art are considered to be within the scope of the present invention. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF THE DRAWINGS

FIG. 1A provides a graph of results of QrtPCR of ASPA mRNA (normalized to 18SrRNA) expressed as a fold-change relative to normal. FIG. 1B provides in silico data from the NCI Rembrandt database, confirming the QrtPCR results. FIG. 1C provides results of densitometric analysis of ASPA western blot (normalized to actin) showing decreased protein expression. [n=4 normal for qPCR & 6 for western blot; for qPCR and western blot: 4 each grade II, grade III and recurrent oligodendroglioma; pilocytic astrocytoma, and 10 GBM. Data are mean±SEM. $*p<0.05$, $**p\le0.01$, $\#p\le0.001$, $\#\#p<0.0001$.]

FIGS. 2A and 2B show results in normal human brains (less than 12 hours post-mortem). FIGS. 2C and 2D show results from glioblastoma multiforme (GBM) tissues; FIGS. 2E and 2F show results in Grade II oligodendroglioma tissues; FIGS. 2G and 2H show results in Grade III oligodendroglioma tissue. ASPA expression was reduced more in glioblastoma multiforme (GBM, grade IV astrocytoma) and grade III oligodendroglioma (GIII Oligo) than in grade II oligodendroglioma Oligo). ASPA was expressed in GFAP positive astrocytes in normal brain (arrowheads), but not in reactive astrocytes in GBM. [Scale bar=50 µm]

FIG. 3 shows a graph and photomicrograph indicating that ASPA regulates glioma cell growth and migration.

FIG. 4 shows graphs and photomicrographs demonstrating effects of N-acetylaspartate (NAA) and N-acetylaspartylglutamate (NAAG) on oligodendroglioma stem cell growth. FIGS. 4A and 4B utilize OG35 and OG33 cells, respectively, and show results when the stem cell spheres were dissociated and treated with 100 µM NAA or 10 µM NAAG in stem cell medium (SCM; DMEM/F12, B27, 20 ng/ml ea bFGF & EGF) or differentiation medium (DM; DMEM, 10% FBS). The cell numbers were determined by manual counting. OG35 cell growth was increased in SCM and DM, while OG33 growth was only increased in SCM. FIG. 4C shows that after 5 days in DM, ASPA localization was largely unaltered by NAA or NAAG with nuclear expression in OG35 and cytosolic expression in OG33. Scale bar=50 $*p<0.05$, n=3, duplicate wells.

FIG. 5 shows graphs, blots, and photomicrographs depicting results that GTA induces oligodendroglioma stem cell growth arrest.

FIG. 6 provides graphs, Western blots, and photomicrographic images showing that GTA induces astrocytoma stem-like cell growth arrest. FIG. 6A shows cell cycle profile graphs showing the percentage of cells in glioma stem-cell like cell (GSC) spheres that were in $G_0/G_1$ or S after growth in SCM and treatment with 0.25% GTA for 24 hrs. All lines, but GBM8, show growth arrest. n=3. FIG. 6B provides graphs showing cell growth as determined by unbiased trypan blue exclusion based cytometry. Although GTA did not induce growth arrest in SCM, it reduced growth in differentiation medium (DM, DMEM, 10% FBS). n=4-6. FIG. 6C shows Western blots (25 µg whole cell lysates) of untreated non-adherent (spheres) or adherent (plated onto poly-L-lysine) GSCs after 24 hrs in SCM and after 1-3 days in DM. Reduced GTA responsiveness in GBM8 could be due to greater ASPA expression in this line. Growth in DM not only increased GFAP expression, but was also associated with nuclear ASPA expression in GBM8 cells, supporting a role for nuclear ASPA in GSC differentiation. Data are mean±SEM. $*p<0.05$, $**p\le0.01$, $\#p\le0.001$, $\#\#p\le0.0001$.

FIG. 7A shows that GTA synergizes with temozolomide (TMZ) to promote survival of mice engrafted with OG35 oligodendroglioma GSCs. FIG. 7B shows that GTA alone increases survival of mice engrafted with GBM12 astrocytoma GSCs as well as synergizing with TMZ.

DETAILED DESCRIPTION

Figure 1:
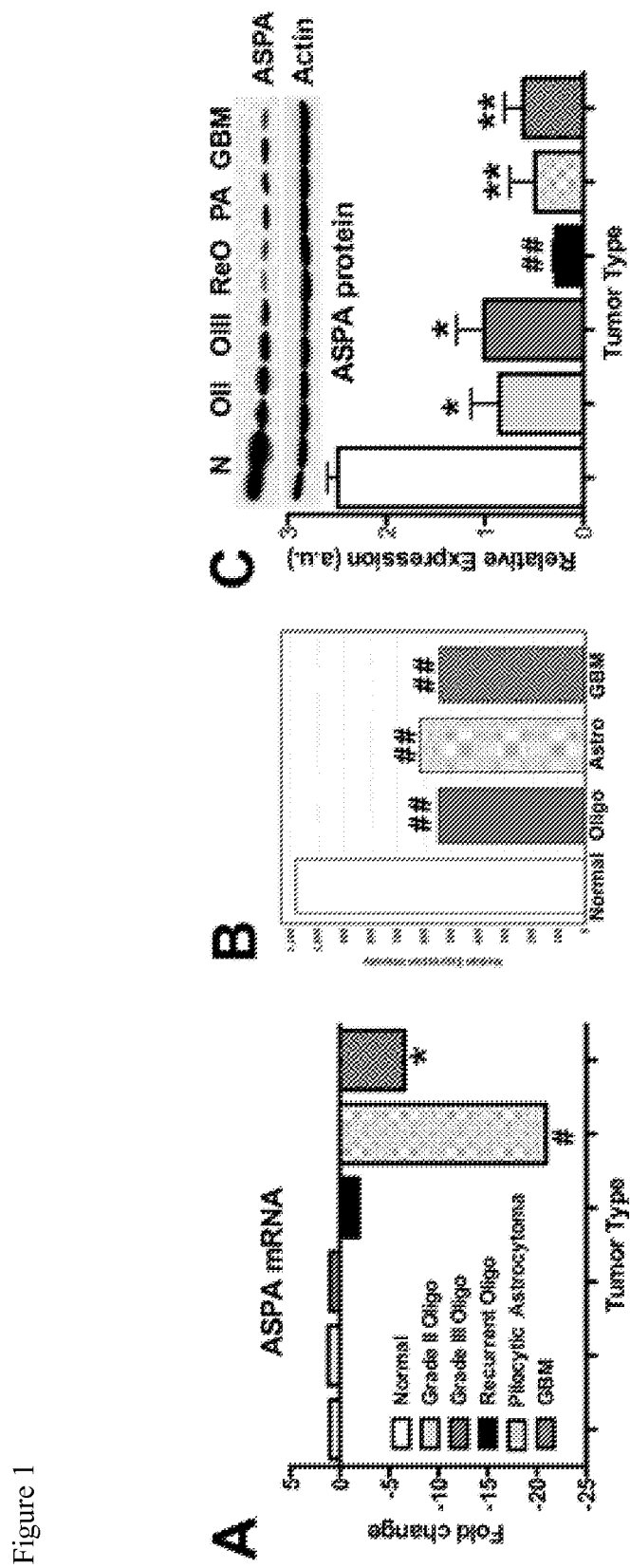
FIG. 1 shows graphs and photomicrographic images demonstrating that aspartoacylase (ASPA) expression was down regulated in glioma in vivo.
Figure 2:
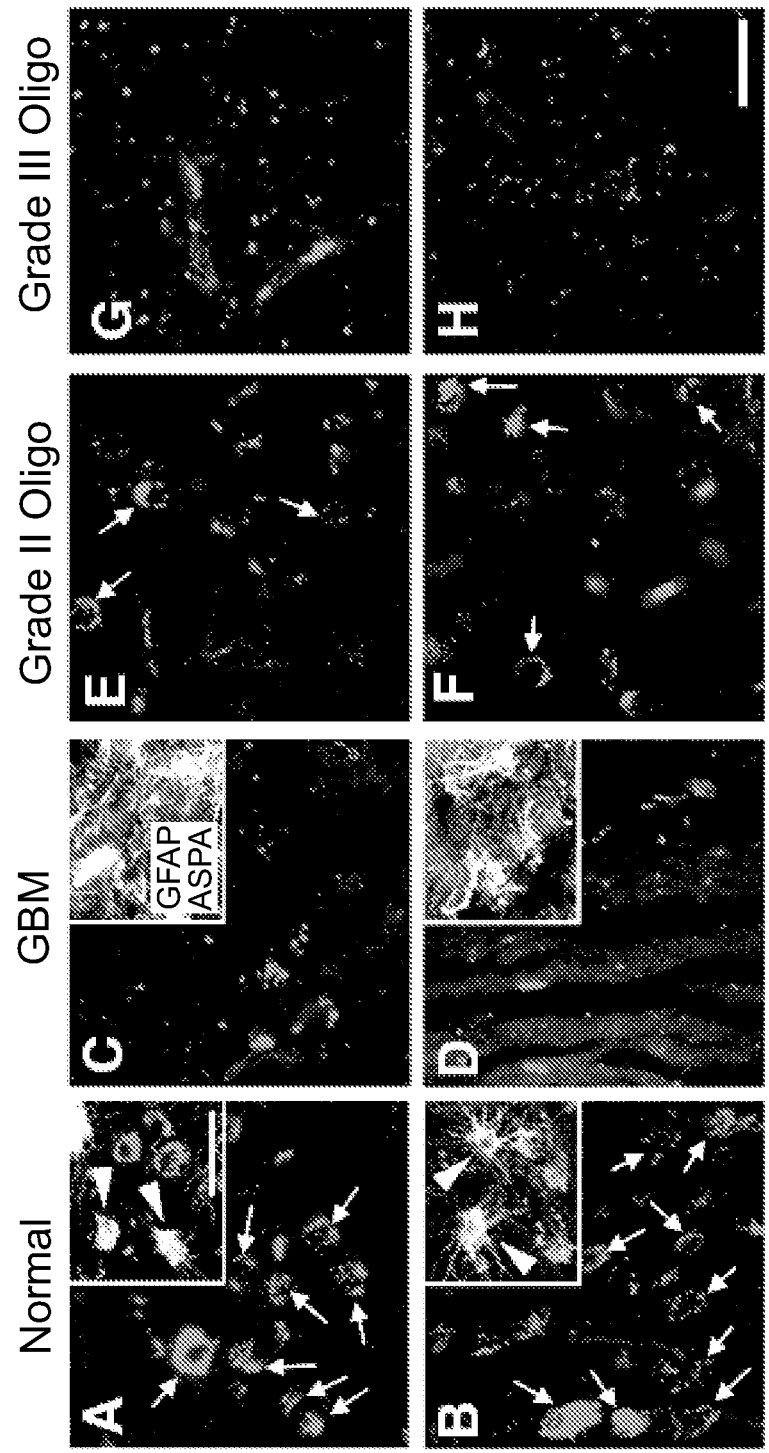
FIG. 2 provides photomicrographic images showing representative immunohistochemistry (IHC) of ASPA expression in two independent tissue samples.

It has now been discovered that glyceryltriacetate (GTA) can reduce cancer cell growth. In addition, it has been found that contacting a cancer stem cell with a GTA compound can result in the differentiation of the cancer stem cell, which limits cancer growth and can lessen chemotherapy resistance of cancer cells. GTA has been previously used as a food additive and as a carrier or solvent in some pharmaceutical agents, perfumes, flavors, etc. It has now been discovered that when administered to a subject at an effective dosage, a GTA compound is effective to treat cancers, including, but not limited to gliomas, neuroblastomas, melanomas, etc.

The invention, in part, also includes the administration of compounds that enhance the cytosolic-nuclear shuttling of ASPA and/or acetyl-CoA synthetase 1 (AceCS1) in cells to treat cancer and reduce cancer cell growth. In some aspects the invention relates to a method of treating cancer involving the administration to a subject having cancer or at risk of having cancer an effective amount of a compound that enhances the cytosolic-nuclear shuttling of ASPA and/or AceCS1 to treat the cancer. In some embodiments, a compound that enhances the cytosolic-nuclear shuttling of ASPA and/or AceCS1 to treat the cancer is a GTA compound. Thus, in some embodiments, methods of the invention include the administration of glyceryltriacetate (GTA) to a subject having cancer or at risk of having cancer an effective amount to treat the cancer. Treatment methods of the invention may, in some embodiments, also include administration of GTA prior to, in conjunction with, or following a therapeutic regimen that includes one or more cancer therapies such as chemotherapy, radiation, surgery, etc. In some embodiments, a subject treated with a method of the invention is a subject that has, or is at risk of having a cancer. Non-limiting examples of a cancer that can be treated using methods of the invention is a glioma, a melanoma, a neuroblastoma, etc.

Glioma, the most common primary adult brain tumor, is associated with a poor prognosis. Median survival of patients with anaplastic oligodendroglioma or glioblastoma multiforme is 14 months. Some patients derive no benefit from temozolomide (TMZ) chemotherapy based on their genetic background (e.g., no 1p/19q LOH or MGMT methylation, respectively). Even with extensive surgical resection, high-grade gliomas are essentially incurable due to recurrence, owing to the highly invasive nature of glioma cells and the persistence of chemoradiotherapeutic resistant glioma stem cells (GSCs) that re-propagate tumors. These recurrent tumors are even more refractory to therapy. It has now been identified that reduced acetate bioavailability contributes to gliomagenesis and acetate supplementation can be used as a therapeutic and preventative approach for gliomas and for other cancers.

It has now been identified that GTA, which is also an FDA-approved food additive, can be administered to treat glioma and other cancers. GTA has now been found to induce GSC growth arrest and differentiation in vitro. GTA increases brain acetate levels, attenuates neuroinflammation, and increases brain histone acetylation by inhibiting HDAC activity. The administration of GTA can be used in methods to treat cancers. Methods of the invention can be used to restore the level of acetate bioavailability and can provide a safe and efficacious means to reduce cancer (e.g. glioma, melanoma, etc.) cell growth.

NAA is the major storage form of brain acetate. ASPA catalyzes NAA to aspartate, which is used in protein synthesis, and acetate, which is the converted to acetyl-coenzyme A via cytosolic/nuclear AceCS1 and mitochondrial AceCS2 for lipid biosynthesis, histone acetylation, and the TCA cycle. NAA levels and ASPA expression are decreased in glioma. Although acetyl-CoA may also be derived from citrate, decreased ASPA mediated NAA catalysis diverts citrate from the TCA cycle and promotes aerobic glycolysis ("Warburg effect"). NAA/ASPA/AceCS1 nuclear localization may also have a role in histone acetylation. Although not intending to be bound by any theory, it is believed that treatment of cancers with GTA may act, at least in part, to enhance the cytosolic-nuclear shuttling of ASPA and/or AceCS1, which can increase cancer cell differentiation and/or decrease cancer cell proliferation. Acetate depletion is associated with transcriptional repression (i.e., deacetylated histones) and enhanced glycolytic metabolism. Administered GTA can be a hydrophobic acetate source that crosses the blood-brain barrier. GTA has been used for acetate supplementation in children with Canavan Disease (CD), a leukodystrophy due to ASPA mutation, without any adverse effects.

It has now been identified that GTA promotes growth arrest and differentiation of GSCs to a greater extent than normal neural stem cells. GTA also enhances the cytosolic-nuclear shuttling of ASPA and AceCS1. These findings support the use of GTA administration as a safe and efficacious chemotherapeutic adjuvant for cancer therapy (including but not limited to glioma therapy) via its dual roles in histone acetylation and metabolism.

Although not wishing to be bound by any particular theory, administered GTA may effect treatment of a cancer via an epigenetic mechanism resulting in cytostasis by promoting histone acetylation and transcriptional activation of differentiation genes and chemotherapeutic adjuvant effects by creating an open chromatin state that permits additional chemotherapeutic agents (for example, TMZ or other cancer chemotherapeutic agent) to have increased access to DNA. The increased access by the additional chemotherapeutic agents increases their efficacy as a cancer treatment. Additional chemotherapeutic agents may be agents that are not glyceryltriaceteate, and thus may be referred to herein as non-glyceryltriacetate chemotherapeutic agents. Examples of additional chemotherapeutic agents (also referred to as non-glyceryltriacetate chemotherapeutic agents) include, but are not limited to: temozolomide, (e.g. Temodar), bevacizumab (e.g., Avastin), bis-chloroethylnitrosourea (BCNU), Lomustine, (e.g., CCNU, belustine, Ceenu), procarbazine, and vincristine, etc.

The invention in some embodiments, pertains at least in part, to increasing acetate bioavailability to treat cancer, i.e., to disrupt the abnormal growth and proliferation of cancer cells. Thus, compositions, compounds, and methods of the invention may be useful in the treatment of a subject having or at risk of having cancer. A subject shall mean a human or vertebrate mammal including but not limited to a dog, cat, horse, goat and primate, e.g., monkey. Thus, the invention can also be used to treat diseases or conditions in non-human subjects. For instance, cancer is one of the leading causes of death in companion animals (i.e., cats and dogs). In some embodiments of the invention, the subject is a human. In some embodiments of the invention, the subject does not have Canavan disease. In some embodiments, the subject is not undergoing a treatment with glyceryltriacetate for a non-cancer indication. In some embodiments, the subject is not undergoing a treatment of a non-cancer indication with an amount of glyceryltriacetate effective to treat a cancer. In certain embodiments, the subject is free of any indications otherwise calling for treatment with glyceryltriacetate. For example, in some embodiments of the invention, a treatment of the invention may be administered to a subject who does not have a non-cancerous indication that would lead to administration of one or more doses or amounts of glyceryltriacetate effective to treat a cancer.

As used herein, the terms "treat", "treated", or "treating" when used with respect to a disorder such as cancer refers to a prophylactic treatment that increases the resistance of a subject to development of the disease or, in other words, decreases the likelihood that the subject will develop the disease, and also refer to a treatment after the subject has developed the disease in order to fight the disease, prevent the disease from becoming worse, or slow the progression of the disease compared to in the absence of the therapy.

A subject at risk of developing a cancer is one who has a high probability, and/or higher than normal probability of developing cancer. These subjects include, for instance, subjects having a genetic abnormality, the presence of which has been demonstrated to have a correlative relation to a higher likelihood of developing a cancer; subjects having a family and/or personal medical history of cancer; subjects exposed to cancer causing agents such as tobacco, asbestos, or other chemical toxins, and/or subjects who have previously been treated for cancer and are in apparent remission. A subject at risk of having cancer also includes a subject having precancerous lesions. A precancerous lesion is an area of tissue that has altered properties and carries the risk of turning into a cancer. Precancerous lesions may be caused by, for instance, genetics and/or exposure to carcinogens such as toxins, chemicals, UV light, or radiation. A subject at risk of developing a cancer that may be treated using a method or compound of the invention may be a subject who has been diagnosed with a cancer that has not yet been determined to have metastasized. Thus, as a non-limiting example, a subject diagnosed with melanoma may be at risk of having a metastasis of the melanoma develop in the brain, and such a metastatic tumor may be suitable for treatment with a method or GTA compound of the invention.

A subject having a cancer is a subject that has detectable cancerous cells. The cancer may be a malignant or non-malignant cancer. Cancers or tumors include but are not limited to benign and malignant tumors; gliomas [for example, ependymoma; astrocytoma, (e.g, pilocytic astrocytoma, glioblastoma multiforme); oligodendroglioma, oligoastrocytoma, gliomatosis cerebri, Choroid plexus papilloma, dysembryoplastic neuroepithelial tumor, medulloblastoma, and Primitive neuroectodermal tumor, etc.]; neuronal cancer [for example, ganglioneuroma, neuroblastoma, atypical teratoid rhabdoid tumor, retinoblastoma, esthesioneuroblastoma, nerve sheath tumors such as neurofibroma (e.g., neurofibrosarcoma, neurofibromatosis, etc.); schwannoma, neurinoma, acoustic neuroma, and neuroma, etc.); leukemias and lymphoid malignancies; biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g., small cell and non-small cell); melanoma; oral cancer; ovarian cancer; pancreas cancer; prostate cancer; rectal cancer; sarcomas; skin cancer; testicular cancer; thyroid cancer; and renal cancer, as well as other carcinomas and sarcomas. In some embodiments the cancer is a glioma. Non-limiting examples of types of gliomas include: astrocytomas, ependymomas, oligodendrogliomas, and mixed gliomas. In some embodiments of the invention, the cancer is a cancer in which ASPA and/or NAA expression and/or activity are decreased compared to non-cancer levels of ASPA and/or NAA expression and/or activity, respectively.

In some embodiments methods of the invention may be used to treat a primary tumor and/or to treat a secondary or metastatic tumor. A metastatic tumor may in a region removed from the primary tumor from which the secondary tumor originated. As a non-limiting example, a metastasis of a melanoma in a subject may localize in the brain and in some embodiments of the invention, a GTA compound may be administered to a subject in an amount effective to treat the secondary tumor (metastasis) in the brain. Thus, in some embodiments, methods of the invention can be used to treat metastatic melanoma. An additional non-limiting example of use of GTA compound in a treatment of the invention may be to administer a GTA compound to a subject to treat a glioma primary tumor in the subject.

GTA is an example of a compound of the invention that when administered in an effective amount to a subject in need of treatment of a cancer can treat the cancer. Treatment of the cancer by GTA may result from an increase the activity of ASPA and/or AceCS1 in cells of a subject having or at risk of having cancer. Administration of GTA may reduce cancer progression and/or may also provide additional energy to subject having cancer. In some embodiments, a compound of the invention may act in a synergistic manner with one or more cancer therapeutic agents and increase the activity of the one or more therapeutic (e.g., chemotherapeutic) agents. Thus, for example, GTA may act synergistically to increase the activity of one or more chemotherapeutic agents (for example, TMZ, or another chemotherapeutic agent set forth elsewhere herein, or known in the art) that can be administered to treat cancer.

Although not intending to be bound by any particular theory, it is believed that cancers in which cells have reduced cytosolic-nuclear shuttling of ASPA and/AceCS1 can be treated with administration of compounds that increase cytosolic-nuclear shuttling of ASPA and/or AceCS1. Thus, according to one set of embodiments of the invention, cancer cells can be exposed to one or more compounds that enhance (e.g., increase) cytosolic-nuclear shuttling of ASPA and/or AceCS1 as a treatment for cancer. As used herein, some compounds of the invention may act to increase the activity of ASPA and/or AceCS1 in a cell by an order of magnitude or more.

Compounds that enhance ASPA and/or AceCs1 activity may also increase oxidative phosphorylation in cells, which may increase cellular generation of $CO_2$. Thus, administration of a compound of the invention may increase acetyl CoA and shift cells from carrying out aerobic glycolysis processes (Warburg effect) to carrying out more oxidative phosphorylation processes. Such a switch may lead to generation of additional CO, by the cells and may result in hyperventilation by the subject to blow off the additional CO, that is produced. This shift to a higher level of oxidative phosphorylation may provide increased energy to a subject undergoing a treatment method of the invention with a compound of the invention, such as but not limited to GTA. Thus, in some aspects, the invention includes methods to increase energy in subjects through administration of such compounds, for example, a GTA compound.

In some embodiments of the invention, a compound administered to treat a cancer is a GTA compound. A GTA compound comprises glyceryltriacetate. GTA is a triglyceride 1,2,3-triacetoxypropane and is also known at least as triacetin; glyceryltriacetate, glycerin triacetate; 1,2,3-propanetriyl triacetate; Enzactin; Fungacetin, Glycerin triacetate; Triacetylglycerol; glycerol triacetate; Glyped; kesscoflex TRA; Tracetine; Vanay, Glycerol triacetate tributyrin; triacetyl glycerine; and Propane-1,2,3-triyl triacetate. In some embodiments, a GTA compound has the molecular formula $(CH_3COOCH_2)_2CH(O_2CCH_3)$ and has the following structure:

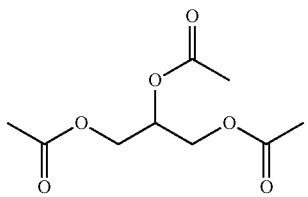

Additional compounds can be identified and used in methods of the invention. For example, candidate compounds can be tested for their ability to increase cytosolic-nuclear shuttling of ASPA and/or AceCS1) and/or for their ability to treat a cancer using standard assays and methods.

Compounds of the invention (such as GTA) described herein can be used alone or in conjugates with other molecules such as targeting agents, labeling agents, delivery agents, and/or cytotoxic agents in treatment methods of the invention.

Targeting agents useful according to the methods of the invention are those that direct a compound of the invention to a site of abnormal proliferation such as a tumor site. The targeting compound of choice will depend upon the nature of the tumor or the tissue origin of the metastasis. In some instances it may be desirable to target the agent to the tissue in which the tumor is located using markers specific to particular tissues or cancer types. Those of ordinary skill in the art will be aware of and able to select and use suitable targeting agents for use in methods of the invention. A non-limiting example of a targeting agent is an antibody against a cancer stem cell antigen.

In some aspects of the invention, a delivery agent may be an agent that permits a compound of the invention (such as GTA) to cross the blood brain barrier. A compound of the invention (such as GTA) can enter the brain in the absence of a specific brain delivery agent because sufficient dosing of GTA may result in a natural osmotic drive that permits GTA to cross the blood brain barrier.

Compositions, compounds, and methods of the invention can be enhanced by utilization in combination with other procedures for cancer and precancerous lesions. In some instances the treatment procedure involves administration of another therapeutic agent such as an anti-cancer agent, including but not limited to chemotherapeutic agents and radiation. In some embodiments, treatments of the invention may also be combined with surgical treatments for the cancer such as tumor removal, debulking, etc. Chemotherapeutic agents may be selected from the group consisting of bevacizumab (e.g., Avastin), bischloroethylnitrosourea (BCNU), Lomustine, (e.g., CCNU, belustine, Ceenu), procarbazine, methotrexate, vincristine, adriamycin, cisplatin, taxol, paclitaxel, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS famesyl transferase inhibitor, famesyl transferase inhibitor, MMP, dacarbazine, LY294002, PX866, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, InceINX-710, VX-853, ZD0101, IS 1641, ODN 698, TA 2516/Marmistat, BB2516/Marmistat, CDP 845, D2163, PDI 83805, DX8951f, Lemonal DP 2202, FK 317, Picibanil/OK-432, AD 32Nalrubicin, Metastron/strontium derivative, Temodal/Temozolomide, temozolomide (TMZ, Temodar), Evacetllipsomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, EniluraciU776C85/5FU enhancer, Campto/Levamisole, Camptosaillrinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dobstain, Caetyx/liposomal doxorubicin, Gemzar/Gemcitabine, ZD 0473/Anormed, YM 116, Iodine seeds, CDK4 and CDK2 inhibitors, PARD inhibitors, D4809/Dexifosamide, Ifes/Mesnex/Ifosamide, Vumon/Teniposide, Paraplatin/Carboplatin, PlantinoVcisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Mechlorethamine HCl (nitrogen mustard), Mercaptopurine, Mesna, Mitotane), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate, but it is not so limited.

In some aspects of the invention, the treatment with a GTA compound and an additional chemotherapeutic agent results in a synergistic effect. Thus, the effect of the combination treatment may be more than an expected additive effect of the GTA compound and therapeutic agent when given in combination.

In some embodiments of the invention, administration of a compound of the invention (e.g., administration of GTA) may be performed in conjunction with therapies for treating the cancer such as surgery and radiation. Treatment methods of the invention that include administration of GTA can be used at any stages of pre-cancer or cancer, including, but not limited to early-stage cancer, mid-stage, and late-stage cancer and all times before and after any of these stages. Methods of the invention may also be used as a "salvage" therapy, for subjects who have previously been treated with one or more chemotherapy, surgical, and/or radiation method that was not successful, and/or is no longer successful at slowing or stopping progression of the cancer in the subject.

The compounds of the invention, (such as GTA, etc.) are administered to the subject in an effective amount for treating cancer. An "effective amount for treating cancer" is an amount necessary or sufficient to realize a desired biologic effect. For example, an effective amount of a compound of the invention could be that amount necessary to (i) kill a cancer cell; (ii) inhibit the further growth of the cancer, i.e., arresting or slowing its development; (iii) sensitize a cancer cell to an anti-cancer agent or therapeutic; (iv) reduce the metastatic potential of a cancer, and/or (v) shrink a tumor, etc. According to some aspects of the invention, an effective amount is that amount of a compound of the invention alone or in combination with a cancer medicament, which when combined or co-administered or administered alone, results in a therapeutic response to the cancer, either in the prevention or the treatment of the cancer. The biological effect may be the amelioration and or absolute elimination of symptoms resulting from the cancer. In another embodiment, the biological effect is the complete abrogation of the cancer, as evidenced for example, by the absence of a tumor or a biopsy or blood smear which is free of cancer cells.

The effective amount of a compound of the invention in the treatment of a cancer or in the reduction of the risk of developing a cancer may vary depending upon the specific compound used, the mode of delivery of the compound, and whether it is used alone or in combination with additional therapeutic methods and/or chemotherapeutics. The effective amount for any particular application can also vary depending on such factors as the cancer being treated, the particular compound being administered, the size of the subject, or the severity of the disease or condition. One of ordinary skill in the art can empirically determine the effective amount of a particular compound of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

Subject doses of the compounds of the invention, (e.g., GTA, etc.) described herein typically range from about 0.1 g to 500 g/day, from 0.5 g to 500 g/day, from 1.0 g to 500 g/day, from 10 to 500 g/day. Thus, the total amount administered to a subject per day (e.g., within 24 hours) in a method of the invention may be at least: 0.1, 0.5, 1.0, 5, 10, 25, 30, 35, 40, 45, 50, 60, 70, 80, 90, 100, 125, 150, 175, 200, 250, 300, 350, 400, 450, 500 or more grams of the GTA compound, including all values and ranges in between the top and bottom of the range set forth. Stated in terms of subject body weight, typical dosages may range from about 0.1 to 0.5 g/kg/day, 0.5 to 5 g/kg/day, 1 to 5 g/kg/day, 0.5 to 10 g/kg/day, 1 to 50 g/kg/day, 10 to 50 g/kg/day, 5 to 100 g/kg/day, 10 to 100 g/kg/day, 10 to 500 g/kg/day, or 50 to 500 g/kg/day, etc.

The amount of a GTA compound administered to a subject in a single dose may range from 0.01-100 g/kg body weight. Thus single GTA doses may be in the range from 0.01, 0.05, 0.1, 0.5, 1.0, 1.5, 2, 3, 4, 5, 6, 7, 8, 9, 10, 20, 30, 40, 50, 60, 70, 80, 90, up to 100 g/kg body weight, including all amounts and ranges in between the top and bottom of the range set forth.

In some embodiments of the invention a GTA compound may be administered to a subject as a single bolus or across a predetermined time interval. In certain embodiments, a dose of a GTA compound in a treatment of the invention is administered to the subject over a time period of up to 1, 5, 10, 15, 20, 30, 40, 50, 60, 120, 180, 240, 300, 360, 420, 480, 540, 600 or more minutes, including all times in between.

In embodiments of the invention, an amount of GTA compound in a dose administered to a subject as a treatment for a cancer is significantly higher than an amount of GTA suitable for use as a pharmaceutical excipient or carrier, for example, for inclusion in a pharmaceutical product as an excipient or carrier for an active pharmaceutical ingredient. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. In some embodiments, a maximum dose can be used, that is, the highest safe dose according to sound medical judgment.

Dosing may also be determined, in part, based on the type of cancer being treated. For example, melanoma and glioma cancers may be treated with doses that are higher than a dose effective to treat a neuroblastoma.

Multiple doses of compounds of the invention are also contemplated. In some instances, a compound of the invention, (e.g. GTA) can be administered at least daily, every other day, weekly, every other week, monthly, etc. Doses may be administered once per day or more than once per day, for example, 2, 3, 4, 5, or more times in one 24 hour period.

In some embodiments of the invention, a compound (e.g. GTA, etc.) of the invention may be administered with a therapeutic dosage of one or more cancer medicaments in a method of the invention to treat a subject having, or at risk of developing, cancer. In some embodiments of the invention, a compound (e.g. GTA, etc.) of the invention may be administered with a sub-therapeutic dosage of one or more cancer medicaments in a method of the invention to treat a subject having, or at risk of developing, cancer. When the two classes of drugs are used together, the cancer medicament may be administered in a sub-therapeutic dose to produce a desirable therapeutic result. A "sub-therapeutic dose" as used herein refers to a dosage that is less than that dosage that would produce a therapeutic result in the subject if administered in the absence of the other agent. Thus, the sub-therapeutic dose of a cancer medicament is one which would not produce the desired therapeutic result in the subject in the absence of the administration of a compound of the invention. For example, GTA may act synergistically to increase the activity of one or more chemotherapeutic agents that can be administered to treat cancer, and so a sub-therapeutic dose of the cancer medicament may be sufficiently enhanced by the compound of the invention, for example, by administered GTA. Therapeutic doses of cancer medicaments are well known in the field of medicine for the treatment of cancer. These dosages have been extensively described in references such as Remington's Pharmaceutical Sciences, 2006 edition, as well as many other medical references relied upon by the medical profession as guidance for the treatment of cancer.

A variety of administration routes are available. The particular delivery mode selected will depend, of course, upon the particular condition being treated and the dosage required for therapeutic efficacy. Methods of this invention, generally speaking, may be practiced using any mode of administration that is medically acceptable, meaning any mode that produces effective levels of protection without causing clinically unacceptable adverse effects. In some embodiments of the invention, a compound of the invention may be administered as a food additive or supplement. In some embodiments, administration of a compound of the invention, including but not limited to GTA, is oral administration. In certain embodiments of the invention, administration of a compound of the invention, including but not limited to GTA, is intragastric administration, a non-limiting example of which is administration via a feeding tube. In some aspects of the invention, administration includes placing the GTA into a surgical cavity, opening, incision, etc. For example, in some embodiments of the invention administration of one or more doses may include placement of the GTA compound into a surgical resection cavity or incision of a subject. In some embodiments of the invention GTA may be administered to a subject in conjunction with a slow release gel or delivery matrix. In some embodiments of the invention, the GTA in a slow release gel or delivery matrix may be administered into a surgical cavity of a subject. Suitable slow release gels and slow release delivery matrices will be known to those skilled in the art, and some are described elsewhere herein.

Additional modes of administration that can be used include, but are not limited to: enteral, mucosal, percutaneous, and parenteral routes. The term "parenteral" includes subcutaneous, intravenous, intramuscular, intraperitoneal, and intrasternal injection, or infusion techniques. Other routes include but are not limited to nasal (e.g., via a gastro-nasal tube), dermal, vaginal, rectal, and sublingual. Local and delivery routes of the invention may include intrathecal, intragastric, intraventricular, or intracranial. In some embodiments of the invention, a compound of the invention may be placed within a slow release matrix and administered by placement of the matrix in the subject. In some aspects of the invention, a compound (such as GTA, etc.) may be delivered to a cancer cell using nanoparticles coated with an antibody against a cancer stem cell antigen (for examples, against glioma/glioma stem cell antigen) and GTA.

Medicaments that include a glyceryltriacetate compound may be manufactured for the treatment of cancer. The medicaments may be manufactured in numerous forms that are appropriate for administration to a subject. A medicament of the invention may include an effective amount of a GTA compound to treat a cancer and may be a pharmaceutically acceptable composition, which is also referred to herein as a pharmaceutical composition.

Compounds of the invention can be administered by any ordinary route for administering medications or may be administered as a food additive or dietary supplement. For use in therapy, an effective amount of the compounds of the invention can be administered to a subject by any mode that delivers the compound to the affected organ or tissue. "Administering" the pharmaceutical composition of the present invention may be accomplished by any means known to the skilled artisan.

Compounds of the invention may be administered in formulations, which may be administered in pharmaceutically acceptable solutions, which may routinely contain pharmaceutically acceptable concentrations of salt, buffering agents, preservatives, compatible carriers, adjuvants, and optionally other therapeutic ingredients. According to methods of the invention, the compound may be administered in a pharmaceutical composition. In general, a pharmaceutical composition comprises the compound of the invention and a pharmaceutically acceptable carrier. Pharmaceutically acceptable carriers are well known to those of ordinary skill in the art. As used herein, a pharmaceutically acceptable carrier means a non-toxic material that does not interfere with the effectiveness of the biological activity of the active ingredients, e.g., the ability of the GTA to treat the cancer.

Pharmaceutically acceptable carriers include diluents, fillers, salts, buffers, stabilizers, solubilizers and other materials that are well-known in the art Exemplary pharmaceutically acceptable carriers are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Compounds of the invention may be formulated into preparations in solid, semi-solid, liquid, or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants, including, but not limited to slow release matrix implants, degradable implants, shunts, etc.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir, or an emulsion.

Compounds of the invention may be mixed with one or more agents to alter and/or improve taste of the compound. For example, though not intended to be limiting, a compound of the invention such as GTA, which has a bitter taste, may be mixed with a sweetener such as Ora-Sweet® (Paddock Laboratories, Minneapolis, Minn.), (e.g. a flavored syrup) in an amount effective to block or reduce the bitter taste of the compound.

Compounds of the invention may be administered directly to a tissue. In some embodiments, the tissue to which the compound is administered is a tissue in which the cancer is likely to arise. Direct tissue administration may be achieved by direct injection. Compounds may be administered once, or alternatively they may be administered in a plurality of administrations. If administered multiple times, the compounds may be administered via different routes. For example, the first (or the first few) administrations may be made directly into the affected tissue while later administrations may be systemic.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores: Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients (e.g. GTA or other compound of the invention) in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent. Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with or without an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day may be used as needed to achieve appropriate systemic or local levels of compounds.

In yet other embodiments, a delivery vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, optionally biodegradable polymeric matrix disclosed in PCT/US/03307. The polymeric matrix may be in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery that is to be used, typically injection into a tissue or administration of a suspension by aerosol into the nasal and/or pulmonary areas. The polymeric matrix composition can be selected to have both favorable degradation rates and also to be formed of a material that is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the compounds of the invention to the subject. In some embodiments, a matrix may be biodegradable. Matrix polymers may be natural or synthetic polymers. A polymer can be selected based on the period of time over which release is desired, generally in the order of a few hours to a year or longer. Typically, release over a period ranging from between a few hours and three to twelve months can be used. The polymer optionally is in the form of a hydrogel that can absorb up to about 90% of its weight in water and further, optionally is cross-linked with multivalent ions or other polymers.

In general, compounds of the invention may be delivered using the bioerodible implant by way of diffusion, or by degradation of the polymeric matrix. Exemplary synthetic polymers that can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the compound, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775; 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for prophylactic treatment of subjects and for subjects at risk of developing a recurrent cancer. Long-term release, as used herein, means that the implant is constructed and arranged to delivery therapeutic levels of the active ingredient for at least 30 days, 60 days, 90 days or longer. Long-term sustained release implants are well-known to those of ordinary skill in the art and include some of the release systems described above.

Therapeutic formulations of compounds of the invention may be prepared for storage by mixing the compound having the desired degree of purity with optional pharmaceutically acceptable carriers, excipients or stabilizers [Remington's Pharmaceutical Sciences $21^{st}$ edition, (2006)], in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN®, PLURONICS® or polyethylene glycol (PEG).

Kits

Also within the scope of the invention are kits that comprise compositions of the invention and instructions for use. Kits may also be referred to herein as "articles of manufacture". Kits of the invention may include one or more of a compound of the invention such as GTA, etc., that may be used to treat a cancer. Kits containing a compound such as GTA can be prepared for treatment methods of the invention. Components of kits of the invention may be packaged either in aqueous medium or in lyophilized form. A kit of the invention may comprise a carrier being compartmentalized to receive in close confinement therein one or more container means or series of container means such as test tubes, vials, flasks, bottles, syringes, or the like. A first container means or series of container means may contain one or more compounds such as a GTA compound, etc. A second container means or series of container means may include one or more additional chemotherapeutic agents. A third container means or series of container means may contain a targeting label or linker-label intermediate capable delivering a compound of the invention to a cell or tissue.

A kit of the invention may also include instructions. Instructions typically will be in written form and will provide guidance for carrying-out the assay or treatment embodied by the kit and for making a determination based upon that assay or treatment. A kit of the invention may also include instructions for combined administration of a compound of the invention such as GTA and an additional chemotherapeutic agent.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Decreased ASPA Expression Contributes to Glioma Cell Growth

Methods

TaqMan Low Density Arrays (TLDAs) were custom designed to identify the protease expression profile of 4 normal brain (pathology free tissue from patients undergoing surgery for epilepsy), 12 oligodendroglioma, and 12 astrocytoma samples as previously described (Swingler et al. 2009 Arthritis Res Ther 11:R96.). Briefly, 800 ng cDNA was added to 2× TaqMan® No AmpErase UNG PCR Master Mix (Applied Biosystems; Warrington, UK) and was loaded onto each TLDA card. Relative gene quantification was performed using the ABI Prism® 7900 HT sequence detection system (Applied Biosystems) using the following cycling conditions: 50° C. for 2 minutes, 94.5° C. for 10 minutes, then 40 cycles of 97° C. for 30 seconds, and 59.7° C. for 1 minute. The data were analyzed using Excel software. The regulation of ASPA mRNA expression was then verified by quantitative real-time PCR using a TaqMan gene expression assay (Hs00163703_m1; Applied Biosystems; Carlsbad, Calif.) and ribosomal RNA control reagents according to manufacturer's instructions.

SDS-PAGE (25 µg protein from whole cell lysates) and western blotting were performed as previously described (Lluri et al. 2008 Exp Cell Res 314:11-24). Cytosol and nuclear fractions were isolated according to standard protocols. Antibodies: rabbit anti-mouse ASPA (2,000×), (Madhavarao et al. 2004 Comp Neurol 472:318-29) rabbit anti-human ASPA (5,000×; GTX1338; GeneTex, Irvine, Calif.), goat anti-human actin (1,000×, sc-1616, Santa Cruz Biotechnology, Santa Cruz, Calif.), rabbit anti-human GAPDH (5,000×, sc-25778, Santa Cruz Biotechnology, Santa Cruz, Calif.), mouse anti-human histone H1 (250×, sc-8030; Santa Cruz Biotechnology, Santa Cruz, Calif.). Species-specific HRP—(3,000×) conjugated secondary antibodies were obtained from Jackson ImmunoResearch (West Grove, Pa.). Immunocomplexes were visualized by enhanced chemiluminescence (PerkinElmer Life Sciences; Boston, Mass.) and densitometry performed using Quantity One software (Bio-Rad; Hercules, Calif.).

Immunocytochemistry was performed as described (Long, P M, et al., (2011) Int J. Cancer, 129:1322-30.).

Results

The down-regulation of aspartoacylase (ASPA) mRNA in glioma identified by TaqMan® low-density array "degradome" profiling (not shown) was confirmed by QrtPCR (FIG. 1A) and microarray data from the NCI Rembrandt database (FIG. 1B). ASPA protein expression was also decreased in both oligodendroglioma and astrocytoma, with the most significant down-regulation in recurrent oligodendroglioma (FIG. 1C). Because ASPA is enriched in oligodendrocytes, its decreased expression in astrocytoma could simply be due to the reduced presence of oligodendrocytes. However, ASPA is expressed in type-2 astrocytes in vitro [Bhakoo, et al., (2001) J Neurochem 79:211-20] and in GFAP-positive astrocytes in normal human brain, but not GBM (FIG. 2A-H). Immunohistochemistry (IHC) also revealed fewer ASPA-positive cells in oligodendroglioma. These data support a role for decreased ASPA in gliomagenesis, both of astrocytic and oligodendrocytic origin. Down-regulation of ASPA in neuroblastoma was recently reported [Long, P M, et al., (2011) Int J. Cancer, 129:1322-30.].

FIG. 1 illustrates results from this investigation and shows that ASPA expression was down regulated in glioma in vivo. QrtPCR of ASPA mRNA (normalized to 18SrRNA) expressed as a fold-change relative to normal as shown in FIG. 1A. FIG. 1B provides in silico data from the NCI Rembrandt database and confirms results of qPCR of decreased ASPA in glioma. FIG. 1C provides results of densitometric analysis of ASPA western blot (normalized to actin) and blots showing decreased ASPA protein in glioma. FIG. 2A-H shows results of representative immunohistochemistry evaluation of ASPA expression in two independent tissue samples. Normal human brains were less than 12 hours post-mortem. ASPA expression was reduced more in glioblastoma multiforme (GBM) and grade III oligodendroglioma (GIII Oligo) than in grade II oligodendroglioma (GII Oligo). ASPA was expressed in GFAP-positive astrocytes in normal brain (arrowheads), but not in reactive astrocytes in GBM.

Example 2

ASPA Regulates Glioma Cell Growth and Migration

Methods

Generation of Stable Tet-Inducible Cells

Human HOG oligodendroglioma cells (Post & Dawson. (1992) Mol. Chem. Neuropathol. 16: 303-17) were simultaneously transfected with PvuI-linearized pTRE-Tight-B1-DsRed2/ASPA (Clontech, Mountain View, Calif.), ScaI-linearized pTet-ON regulatory plasmid and the linear puromycin selection marker. Puromycin (1 µg/ml)-G418 (2 mg/ml) resistant clones were screened by western blot analysis and immunocytochemistry for homogeneous tight expression comparable to ASPA expression in normal human brain. As a control for potential cytotoxicity of doxycycline or DsRed, HOG cells were also transfected with pTet-ON, puromycin and empty pTRE vector. After selecting stable clones, cells were grown in DMEM (Mediatech), 5% FBS (Hyclone), 1µ/ml puromycin (Clontech, Mountain View, Calif.), 2 mg/ml G418 (Mediatecb, Manassas, Va.), and pen/strep. ASPA expression is induced 24 hours after plating using 1 µg/ml doxycycline (Sigma Aldrich, St. Louis, Mo.).

Cell growth was determined by manual counting following trypsinization and trypan blue labeling. Doxycycline (dox), or fresh media without dox, was added 24 hours after plating and cells fed every 48 hours.

Cell motility was measured using a wound-healing assay. Cells were plated at a density ($5 \times 10^4$ cells/well of 24 well plate) such that on the day of injury (36 hrs after dox induction), the monolayer was absolutely confluent. Prior to making the wound, the growth medium was aspirated and replaced with calcium-free DPBS to prevent cell death at the wound edge due to high calcium concentrations. A scratch wound of approximately 400 µm width was made with a P1000 pipette tip to image the entire width of the wound using a 10× objective. After a 10 min incubation, the well was washed and culture medium added. The wound was imaged 24 hrs after injury.

Loss of heterozygosity in the chromosomal region 17p13.3, near ASPA, is associated with increased cell proliferation in astrocytic tumors [Sarkar, C. et al., (2003) Cancer Genet Cytogenet 144:156-64]. Stable tet-inducible (pTRE-Tight-Bi-DsRed2/ASPA) HOG oligodendroglioma cell lines were generated to test whether ASPA restoration would regulate cell proliferation. DsRed expression began to be detected 24 hours after doxycycline addition, with most cells becoming DsRed-positive by 72 hours. Doxycycline-induced ASPA expression was associated with significantly reduced cell number (FIG. 3A) and migration (FIG. 3B). The actual decrement in cell number was an underestimation since 100% of the cells did not induce DsRed/ASPA expression. In the absence of doxycycline, ASPA transfected cells showed a slight, but not statistically significant, reduction in cell number relative to pTRE vector control cells, most likely due to the presence of cells with "leaky" ASPA expression. These data support a role for ASPA in glioma cell growth.

Figure 3A:
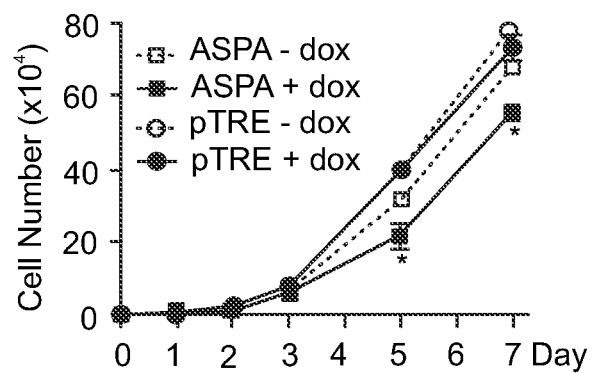
FIG. 3A is a graph showing HOG oligodendroglioma cell number determined by manual counting following trypsinization and trypan blue labeling. Doxycycline, to induce ASPA expression, was added 24 hours after plating. ASPA expression resulted in a significantly reduced viable cell number after 5 days ($*p=0.014$) and 7 days ($*p=0.013$). n=3 pTRE vector alone, n=5 ASPA.
Figure 3B:
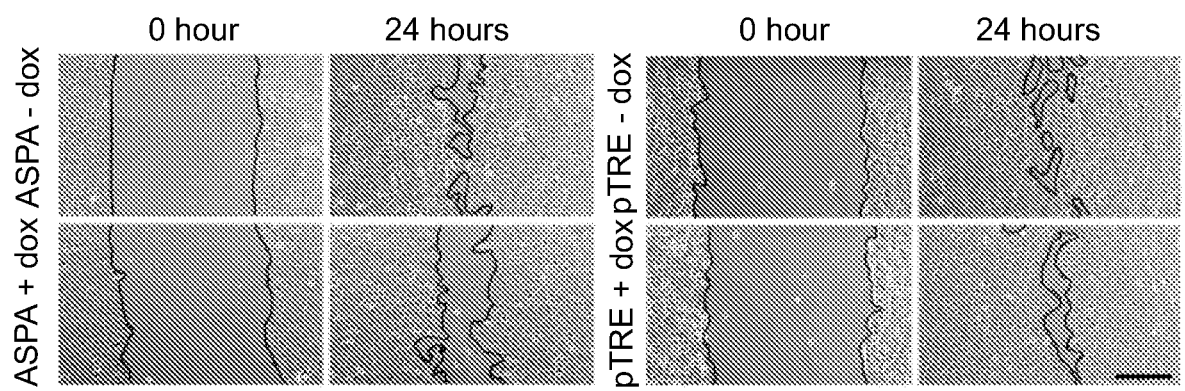
FIG. 3B shows photographs indicating results when confluent HOG cells were injured (24 hours after plating and 36 hours after dox addition) and the extent of "wound" closure, as an indication of cell migration, was determined 24 hours later. ASPA reexpression decreased migration/wound healing. Scale bar=250 µm.

Results of these experiments are illustrated in FIG. 3. FIG. 3A shows results of experiment in which cell number was determined by manual counting following trypsinization and/or trypan blue labeling. Doxycycline was added 24 hours after plating. ASPA restoration resulted in a significantly reduced viable cell number after 5 days. FIG. 3B shows results obtained with confluent HOG cells were injured (24 hours after plating and 36 hours after dox addition) and the extent of wound closure was determined 24 hours later. ASPA re-expression decreased migration/wound healing.

Example 3

NAA Promotes Oligodendroglioma Stem Cell Growth

Methods
Cell Culture

Stem cell spheres from two oligodendroglioma stem cell lines (OG33 and OG35) were plated (at 10,000 cells per well of a 24-well plate) in the absence or presence of 100 µM N-acetylaspartate (NAA) or 10 µM N-acetylaspartylglutamate (NAAG) in stem cell medium (SCM) containing DMEM/F12 (Gibco/Life Technologies, Grand Island, N.Y.), B27 supplement (Gibco/Life Technologies, Grand Island, N.Y.), and 20 ng/ml each basic fibroblast growth factor (bFGF) and epidermal growth factor (EGF), or differentiation medium (DM) containing DMEM, 10% FBS. Medium, with fresh drug, was replenished every 48 hours. Growth dynamics were assessed using trypan blue exclusion and manual counting 1, 3, and 5 days after plating.

Immunocytochemistry was performed as described (Perez-Martinez & Jaworski (2005) J Neurosci 25:4917-29). Briefly, OG33 and OG35 cells were plated into differentiaion medium (DMEM, 10% FBS), fixed with 2% paraformaldehyde, and ASPA expression localized immunocytochemically using rabbit anti-mouse ASPA (1,500×) (Madhavarao et al., 2004 Comp Neurol 472:318-29) and Cy-3 conjugated secondary antibody (500×; Jackson ImmunoResearch, West Grove, Pa.).

NAA is reduced or absent in MRS spectra of brain tumors [Moffett, J R, et. al., (2007) Prog Neurobiol 81:89-131; Barker, P. B., et. al., (2006) In N-Acetylaspartate: A Unique Neuronal Molecule in the Central Nervous System, J. R. Moffett, et al., Editors. Springer: New York. 183-1971], even though oligodendrocytes can synthesize NAA [Bhakoo, K. K., et al., (2000) J Neurochem 74:254-62.29]. Thus, decreased ASPA expression may simply be a consequence of reduced substrate availability. Therefore, whether addition of NAA, ASPA's only known substrate, could restore ASPA expression and negatively regulate cell growth was tested. Because in vitro passaged cancer cell lines often bear little resemblance to the primary tumor from which they were derived and therapies need to target the GSCs in addition to their progeny, two oligodendroglioma stem cell lines (OG33 and OG35) were obtained for this study. Flow cytometric cell cycle analysis revealed that NAAG, but not NAA, promoted OG35 growth (i.e., increased percentage of cells in $G_2/M$ and decreased cells in $G_0/G_1$), but no significant change in OG33 cell number in either NAAG or NAA (not shown). At later time points, however, both OG35 (FIG. 4A) and OG33 (FIG. 4B) cell number was increased, but OG33 cells were only responsive when grown in stem cell medium (SCM) and showed an attenuated response relative to OG35 cells.

NAA and NAAG treatment had little effect on ASPA spatial localization, which was primarily nuclear in OG35 cells and cytosolic in OG33 cells (FIG. 4C). Thus, in contrast to a recent report suggesting that NAA and/or NAAG may serve as tumor suppressors [Reitman, Z. J., et. al. (2011) Proc Natl Acad Sci USA 108:3270-5], these data appear to refute a tumor suppressor role for these amino acid derivatives and contraindicates their therapeutic use in oligodendroglioma.

FIG. 4 illustrates the results of these experiments. FIGS. 4A and 4B show results when stein cell spheres were dissociated and treated with 100 µM NAA or 10 µM NAAG in stem cell medium (SCM; DMEM/F12, B27, 20 ng/ml ea bFGF & EGF) or differentiation medium (DM; DMEM, 10% FBS) and cell number was determined by manual counting. OG35 cell growth was increased in SCM and DM, while OG33 growth was only increased in SCM. FIG. 4C shows that after 5 days in DM, ASPA localization was largely unaltered by NAA or NAAG with nuclear expression in OG35 and cytosolic expression in OG33.

Example 4

GTA-Derived Acetate Promotes Oligodendroglioma Stem Cell Growth Arrest and Differentiation Methods Cell cycle profiles were visualized by propidium iodide (PI) staining as previously described (Perez-Martinez & Jaworski (2005) J Neurosci 25:4917-29). OG35, OG33 and mouse neural stem cells were grown in stem cell medium (SCM; DMEM/F12, B27, 20 ng/ml ea bFGF & EGF) while the oligodendrocyte progenitor cell line, Oli-neu (Jung et al. (1995) Eur J Neurosci 7:1245-65) was grown in Sato's medium (DMEM supplemented with 100 µg/ml apotransferrin, 5 µg/ml insulin, 60 nM triiodothyronine, 30 nM sodium selenite, 100 µM putrescine, 1% horse serum, and 25 µg/ml G418). Twenty-hours hours after 0.25% (v/v) GTA treatment, cells were trypsinized, recovered by centrifugation, re-suspended ($10^6$ cells/ml) in a low-salt PI solution (3 g/ml polyethylene glycol PEG 8000, 50 g/ml PI, 180 U/ml RNase A, 0.1% Triton X-100, and 4 mM sodium citrate), and incubated at 37° C. for 20 minutes. After addition of an equal volume of high-salt PI solution (3 g/ml polyethylene glycol PEG 8000, 50 g/ml PI, 180 U/ml RNase A, 0.1% Triton X-100, and 400 mM NaCl) and incubation at 4° C. for 1 hour, cell cycle profiles were recorded by flow cytometry (BD LSR 11 Flow Cytometer, BD Biosciences; Franklin Lakes, N.J.).

Growth dynamics were assessed using unbiased trypan blue exclusion based cytometry. Cells were plated (at 10,000 cells per well of a 24-well plate) directly in the absence or presence of 0.25% GTA. After 1, 3, and 5 days of treatment, cells were typsinized, collected via centrifugation, and counted according to the manufacturer's instructions (Countess Automated Cell Counter; Invitrogen Life Technologies; Carlsbad, Calif.).

Immunocytochemistry was performed as described (Perez-Martinez & Jaworski (2005) J Neurosci 25:4917-29). Briefly, OG33 and OG35 cells were plated into differentiaion medium (DMEM, 10% FBS) in the absence or presence of 0.25% GAT and fixed with 2% paraformaldehyde after 5 days. Antibodies: rabbit anti-human ASPA (1500×; GTX13389; GeneTex, Irvine, Calif.), Rabbit anti-mouse ASPA (2,000× for western blot) (Madhavarao et al., 2004 Comp Neurol 472:318-29), rabbit anti-mouse AceCS1 (15, 000× western blot; 1,500× immunocytochemistry) (Ariyannur et al. 2010 J Comp Neurol 518:2952-77), rabbit anti-mouse 2',3'-cyclic nucleotide 3'-phosphodiesterase (CNPase; 500×sc-30158; Santa Cruz Biotechnology, Santa Cruz, Calif.). Cy3- (500×) conjugated secondary antibodies were obtained from Jackson ImmunoResearch (West Grove, Pa.). Immunocytochemistry for Histone 3/Tubulin/poly (ADP-ribose) polymerase (PARP) was performed using the PathScan Multiplex IF kit per manufacturer's instructions (Cell Signaling Technology, Danvers, Mass.).

SDS-PAGE (25 µg protein from whole cell lysates) and western blotting were performed as previously described in Example 1.

Results.

Figure 5A:
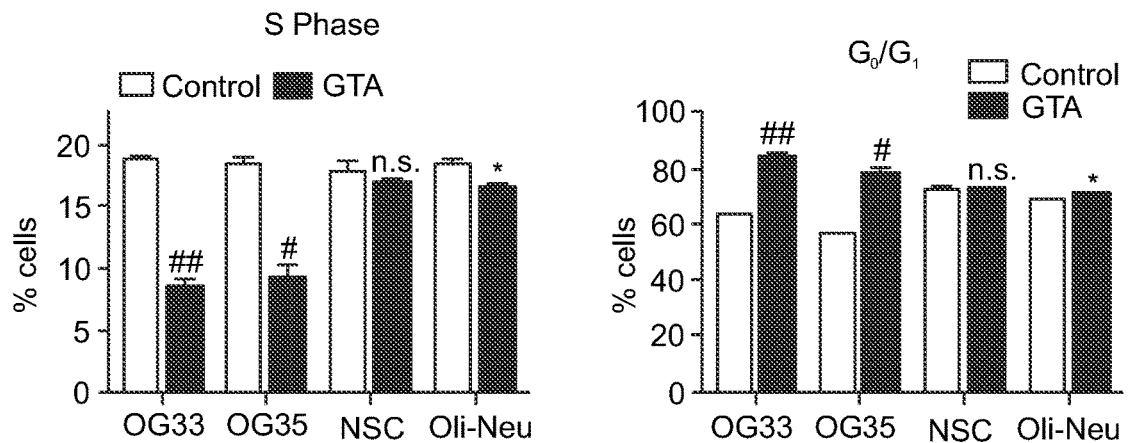
FIG. 5A shows graphs of the cell cycle profile, examined by propidium iodine staining and flow cytometry, of freshly dissociated oligodendroglioma stem cells spheres (0033 and OG35) and murine neural stem cells (NSCs) in SCM (DMEM/F12, B27, 20 ng/ml ea bFGF & EGF), and a murine oligodendrocyte progenitor cell (OPC) line (Oli-Neu) in Sato's media that were treated with 0.25% GTA for 24 hrs. GTA reduced growth (decreased S phase) of gnome stem cells greater than normal OPCs. n=3.
Figure 5B:
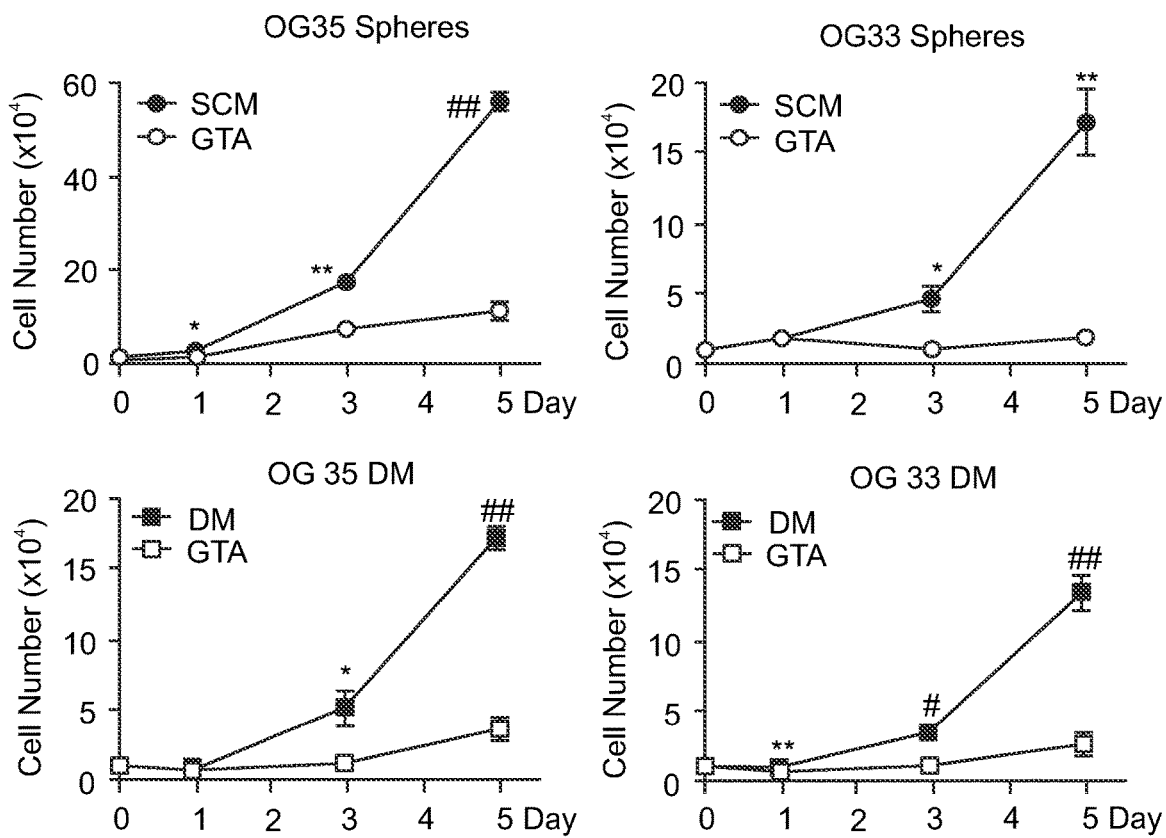
FIG. 5B provides graphs showing cell growth as determined by unbiased trypan blue exclusion based cytometry (cells plated with 0.25% GTA and media with fresh GTA replenished every 48 hrs). n=3-5.
Figure 5C:
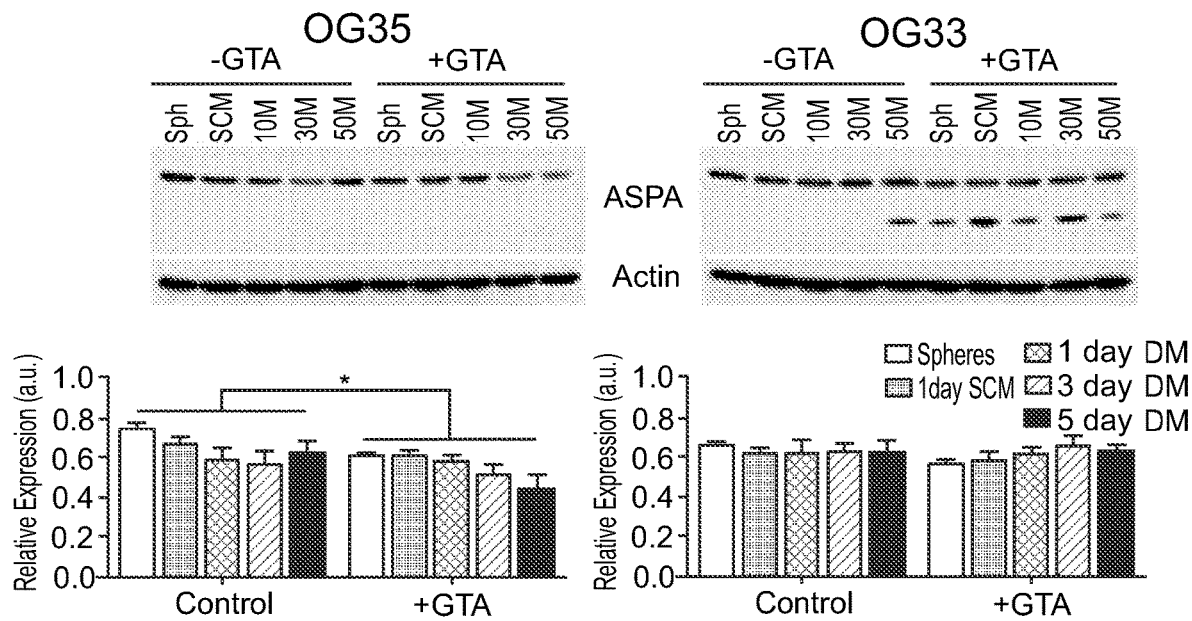
FIG. 5C shows results of Western blot analysis that revealed that GTA treatment reduced ASPA expression in 0035 cells and had no effect on the putative 36 kDa ASPA protein in OG 33 cells. The graphs show quantitative analysis of the Western blot results. A novel 26 kDa species was present not only in GTA treated 0033 cells, but untreated cells after 5 days in DM. n=3.
Figure 5D:
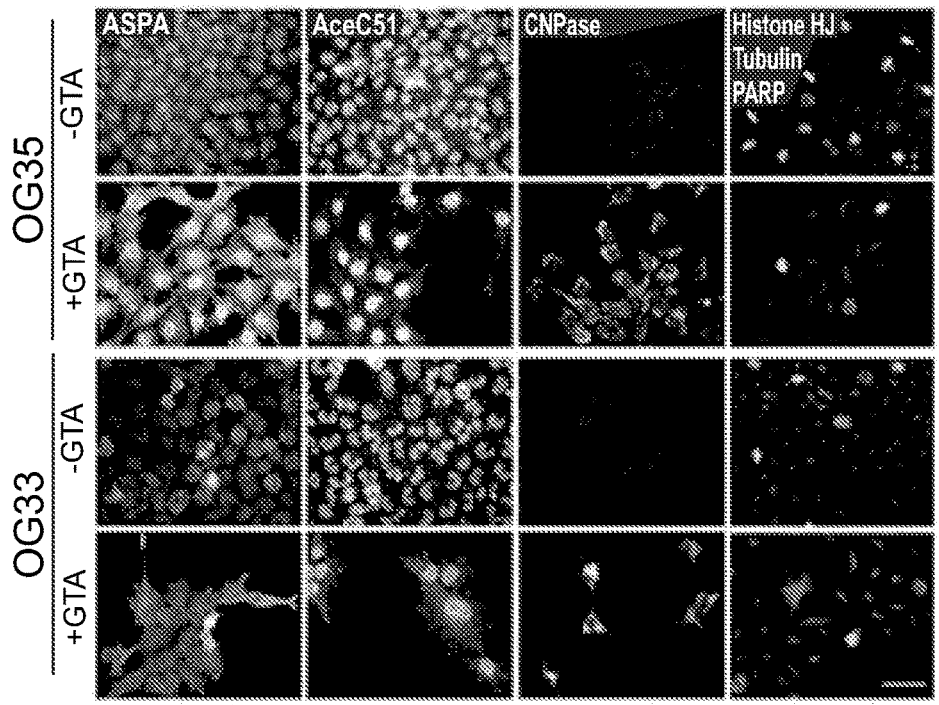
FIG. 5D shows immunocytochemistry (ICC) results after 5 days in the absence or presence of 0.25% GTA. ICC was performed to detect ASPA, AceGS1, CNPase, and Histone 3/Tubulin/PARP for +GTA and −GTA treated OG35 cells and 0033 cells. Reduced cell number was primarily due to less proliferation (decreased phospho-histone H3 [Ser 10]) and not more apoptosis (no cleaved PARP [Poly (ADPribose) polymerase, Asp214] detectable) (PathScan Multiplex IF kit, Cell Signaling). Scale bar=50 µm.
Figure 5E:
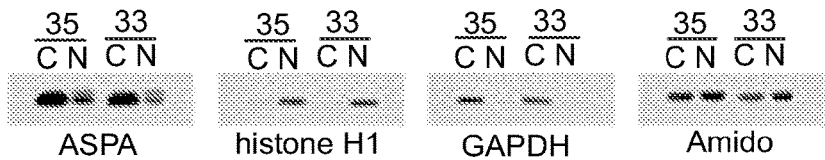
FIG. 5E shows Western blots of cytosolic (C) and nuclear (N) fractions from untreated cells after 3 days in DM and indicates that ASPA was more abundantly expressed in the nucleus of OG35 cells than OG33 cells. Blots were stripped and sequentially probed with histone H1 and GAPDH to demonstrate subcellular fraction purity. Blots were stained with Amido Black to assess loading. Data are mean±SEM. n.s.=not significant, $*p<0.05$, $**p\le0.01$, $\#p\le0.001$, $\#\#p\le0.0001$.

NAA is the major storage form of acetate in the brain and both NAA levels and ASPA expression are decreased in glioma; thus, acetate bioavailability is reduced. Inasmuch as acetate is the end product of ASPA-mediate NAA cleavage, experiments were performed to test whether GTA-mediated acetate supplementation would reduce growth of GSCs derived from human grade II (OG33) and grade Ill (OG35) oligodendroglioma. In contrast to free acetate, GTA is a hydrophobic molecule that can readily cross membranes without an uptake system. Flow cytometry of propidium iodide (PI) labeled cells revealed that 0.25% GTA in stem cell medium (SCM) for 24 hours induced cell cycle arrest of OG33 and OG35 GSCs, but had less effect on Oli-Neu cells, an oligodendrocyte progenitor cell (OPC) line (Jung, M, et al., (1995) Eur J Neurosci 7:1245-65), and no effect on murine neural stem cells (NSCs) (FIG. 5A) and, in contrast to NAA/NAAG (FIG. 4A), 0.25% GTA resulted in significantly decreased cell number after 5 days of treatment (FIG. 5B). Also, GTA decreased ASPA expression in OG35 cells (FIG. 5C), perhaps as an autocrine regulatory mechanism to prevent additional acetate generation via ASPA-mediated NAA cleavage. In contrast, in OG33 cells, GTA had no effect on expression of the putative 36 kDa ASPA protein, but induced the expression of a novel 26 kDa species. Interestingly, this species was not only induced by NAA and NAAG treatment, but also within highly confluent untreated OG33 cultures (not shown). Reduced cell number was primarily due to less proliferation (decreased phospho-histone H3 [Ser 10]) and not more apoptosis (no cleaved PARP [Poly (AD-Pribose) polymerase, Asp214] detectable) (FIG. 5D). GTA did increase the nuclear expression of ASPA in OG35, but not OG33, cells, even though AceCS1 was abundantly expressed in both cell lines. Increased nuclear ASPA/ AceCS1 was associated with GSC differentiation (increased expression of CNPase, a marker of mature oligodendrocytes) primarily in OG35 cells. Western blotting of cytosolic and nuclear fractions confirmed prior immunocytochemical observation that ASPA was more abundant in the nucleus of OG35 cells than OG33 cells (FIG. 5E).

FIG. 5 illustrates the results of these studies. FIG. 5A shows results when freshly dissociated oligodendroglioma stem cells (GSCs) were treated with 0.25% GTA in SCM cell cycle arrest was more pronounced in GTA-treated GSCs than in mouse neural stem cells (NSCs) or oligodendrocyte progenitor cells, Oli-neu. FIG. 5B shows that GTA reduced cell growth dynamics, as determined by unbiased automated counting. FIG. 5C shows Western blot analysis that revealed that GTA treatment reduced ASPA expression in OG35 cells and had no effect on the putative 36 kDa ASPA protein. A novel 26 kDa species was present not only in GTA treated OG33 cells, but untreated cells after 5 days in DM. FIG. 5D shows immunocytochemistry after 5 days in the absence or presence of GTA demonstrating that reduced cell number was primarily due to less proliferation (decreased phospho-histone H3) and not more apoptosis (no cleaved PARD detectable) and that GTA increased the nuclear expression of ASPA in OG35 cells coincident with GSC differentiation (i.e., more CNPase-positive cells). FIG. 5E shows Western blots of cytosolic (C) and nuclear (N) fractions from untreated cells after 3 days in DM demonstrating that ASPA was more abundantly expressed in the nucleus of OG35 cells than OG33 cells. Blots were stripped and sequentially probed with histone H1 and glyceraldehyde 3-phosphate dehydrogenase (GAPDH) to demonstrate subcellular fraction purity. Blots were stained with Amido Black to assess loading.

Example 5

GTA Promotes GSC Growth Arrest and Differentiation In Vitro

Methods

Flow cytometry was performed 24 hours after GTA treatment as described in prior examples herein.

Growth dynamics was determined as described in prior examples herein.

Western Blot analysis and immunocytochemistry were performed on cells grown in the absence of GTA as described in prior examples herein.

Results

Inasmuch as astrocytomas account for 75% of all gliomas, with ~50% being GBM [Adamson, C, et al., (2009) *Expert Opin Investig Drugs* 18:1061-83], GTA's effect on two human GBM-derived GSC lines was examined. GTA exerted growth arrest (increased proportion of cells in $G_0/G_1$ and decreased proportion of cells in S phase) in all GSCs, except GBM8, when treated in SCM for 24 hours (FIG. 6A), but reduced growth dynamics of GBM8 cells in when grown in DM (FIG. 6B). The diminished growth inhibition on GBM8 cells could either be due to greater ASPA expression (FIG. 6C). When grown in DM for 3 days, GBM8, but not GBM12, increased expression of GFAP and CNPase. The ASPA expression was primarily nuclear in the differentiated GFAP$^+$ cells; thus, suggesting that nuclear ASPA plays a role in GSC differentiation.

Example 6

GTA Enhances the Chemotherapeutic Effect of Temozolomide in Orthotopic Grafts In Vivo—GTA Acts Synergistically with TMZ to Promote Survival Methods Cells (2,500 cells in 4 µl) were injected into the right striatum (1 mm anterior, 1.5 mm lateral to bregma, 3.5 mm deep) of adult athymic mice (8-week-old, 25-28 g). GTA (5.8 g/kg plus 10% v/v Ora-Sweet SF® (Paddock Laboratories, Minneapolis, Minn.) was administered intragastrically daily starting on the third post-operative day. TMZ (20 mg/kg) was administered intragastrically in an oral suspension vehicle containing 2.5 mg/ml Povidone K30, 0.013% citric acid, 50% Ora-Plus® (Paddock Laboratories, Minneapolis, Minn.), 50% Ora-Sweet SF® (Paddock Laboratories, Minneapolis, Minn.) on days 5, 7, 9, 11, and 13. Mice receiving the combined GTA/TMZ therapy received the TMZ in the morning (~7-8 AM) and GTA in the evening (~6-7 PM).

For in vivo imaging, mice were injected i.p. with 150 mg/kg D-luciferin potassium salt 5 minutes prior to imaging under 1.5% inhaled isoflurane. Peak efflux was determined from an average of 15 bioluminescent acquisitions, with 1 min inter-acquisition intervals, using the auto-exposure setting. Total photon efflux was determined by drawing regions of interest over the emitted region and setting thresholds for each mouse to maximize the number of pixels encircled using Living Image acquisition and analysis software (Version 3.0.3.5, Caliper Life Sciences, Hopkinton, Mass.). Bioluminescent signals were expressed in units of photons per $cm^2$ per second per steradian ($p/cm^2/s/sr$).

Statistical Analysis

Tumor bioluminescence (rate of flux change over time) and tumor volume were compared using a Mann-Whitney test. Survival was analyzed using Kaplan-Meier curves [Kaplan, EL and P Meier. (1958) *J Am Stat Assoc* 53:457-481] and comparisons between groups were analyzed with a log-rank test [Peto, R and J Peto. (1972) *J R Stat Soc Ser A Stat Soc* 135:185-207].

Results

Figure 7:
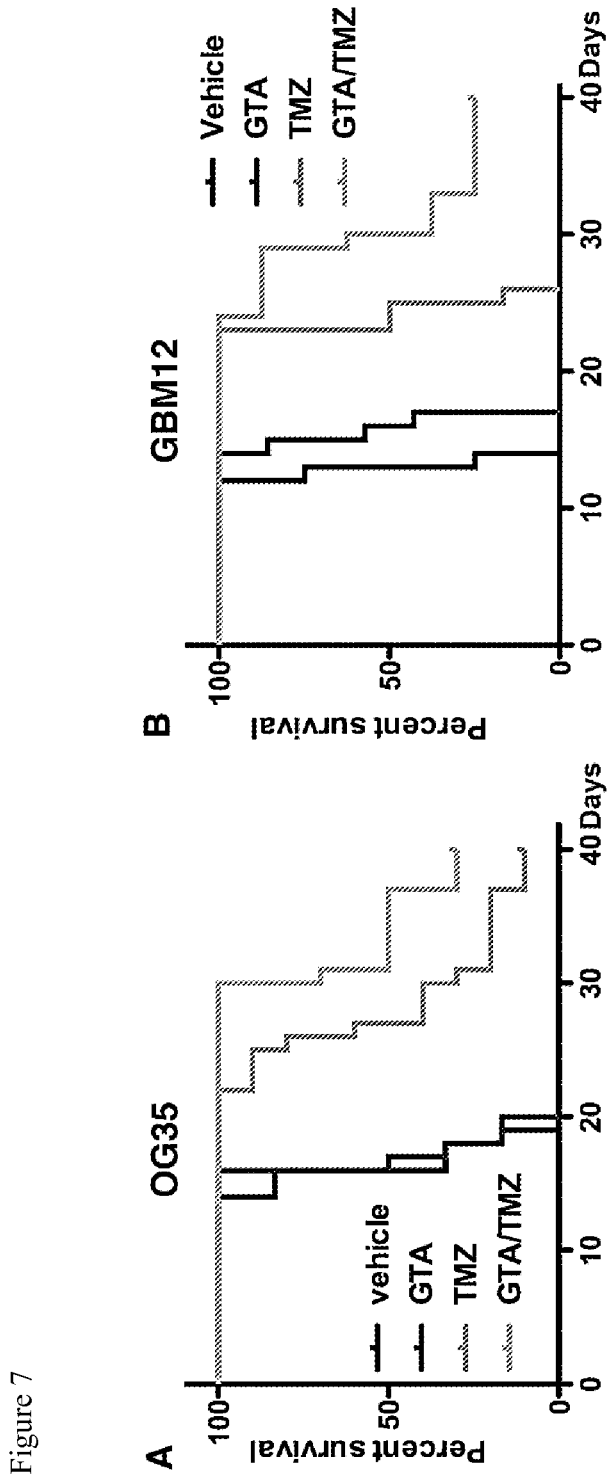
FIG. 7 provides graphs indicating mean survival of mice engrafted with OG35 and GBM12 GSCs.

Given the profound cytostatic effects observed in vitro, tests were performed to determine whether GTA could exert anti-neoplastic activity on orthotopically grafted GSCs and/or synergize with TMZ treatment. Results are shown in FIGS. 7A and 7B. Oligodendroglioma (OG35) and GBM (GBM12) GSCs were transduced using high-titre lentivirus based on pHRs-UkFG in which luciferase is driven under the poly Ubiquitin promoter and cells with viral integration (due to GFP in vector) were isolated by fluorescence activated cell sorting (FACS). Cells were stereotactically injected into the right striatum of adult male athymic mice. Bioluminescent imaging was performed using the Xenogen IVIS 200 imaging system 3 days post grafting, at which time mice were pair matched for treatment (the assignments were negatively biased by assigning the mouse with higher flux to the GTA/TMZ combi therapy group). Mice were imaged twice per week. To test if "priming" with GTA would promote an open chromatin state and/or GSC differentiation to enhance TMZ efficacy, GTA (5.8 g/kg with 10% Ora-Sweet® (Paddock Laboratories, Minneapolis, Minn.) to block GTA's bitter taste) was administered intragastrically 2 days prior to TMZ administration then daily until euthanasia. A single course of TMZ (20 mg/kg in an oral suspension vehicle adapted from Trissel, L A, et al., (2006) Int Pharm Compound 10: 396-399), was administered intragastrically on days 5, 7, 9, 11, and 13. To exclude the possibility that GTA was simply serving as a delivery vehicle for TMZ (e.g., as a "Trojan horse"), mice treated with both GTA and TMZ received TMZ in the morning and GTA in the evening (just prior to lights off active period because GTA increased basal metabolic activity). Although GTA alone did not significantly increase survival, 0035 engrafted mice treated with GTA and TMZ survived longer than those treated with TMZ alone (p=0.03). Furthermore, GTA significantly delayed time to tumor regrowth after, termination of TMZ treatment. The experiment was stopped at 40 days when tumors failed to regrow in 3 of 6 GTA/TMZ treated mice; thus, the survival effect is underestimated in the study and is expected to be greater. In contrast to OG35 engrafted mice, GBM 12 engrafted mice treated with GTA alone had increased survival relative to vehicle treated mice (p<0.0001). Similar to differences in GBM8 and GBM12 GTA responsiveness in vitro, the 0035 tumors may be less responsive to GTA than GBM 12 tumors because the OG35 tumors are more slowly growing. GBM 12 engrafted mice treated with GTA and TMZ survived significantly longer than TMZ alone (p<0.0001). Volumetric tumor measurements (normalized to survival day because combination mice survived longer) are performed.

Example 7

GTA as a Cancer Therapeutic Alone and in Combination with Additional Cancer Therapeutics Methods Orthotopic grafting was performed as described above in Example 6. In addition to the treatments described above, the following treatments were tested: 1) concurrent (GTA and TMZ on days 5, 7, 9, 11, 13, with GTA alone on days 6, 8, 10, 12 and continuous GTA afterwards), and 2) salvage (GTA administered daily after single course of TMZ on days 5, 7, 9, 11, and 13).

Results

Figure 8:
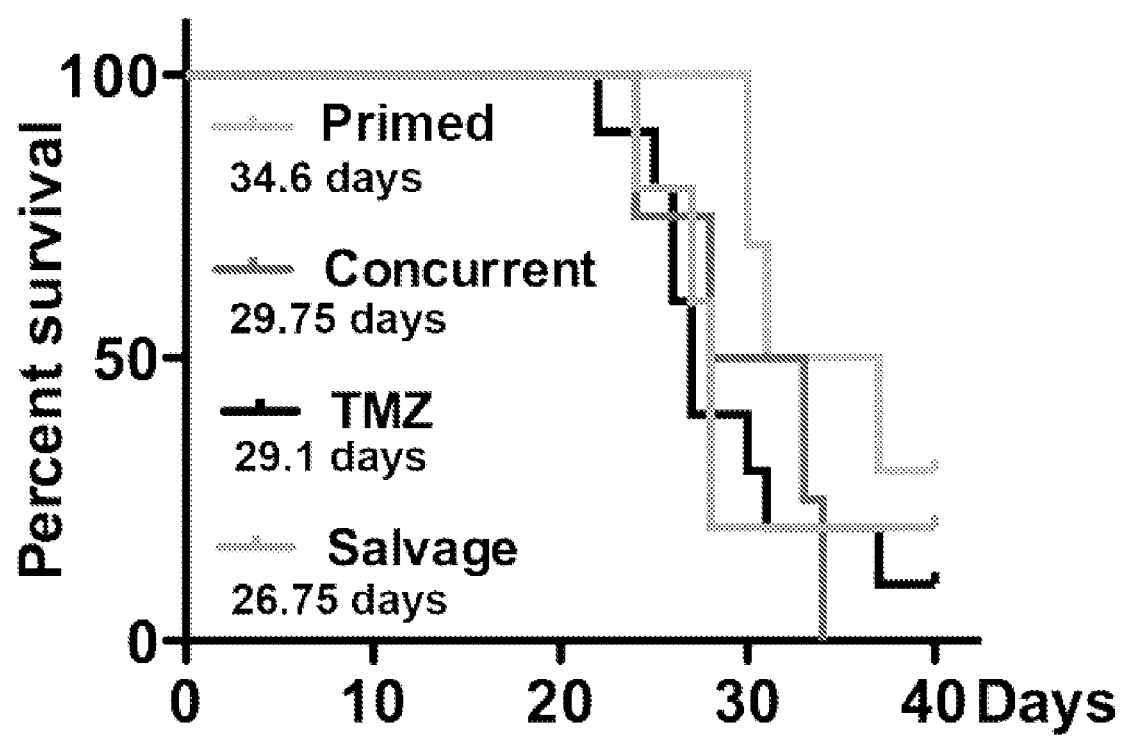
FIG. 8 shows a graph that indicates the optimum treatment regimen for increased survival of mice engrafted with OG35 GSCs. Only priming with GTA two days prior to TMZ treatment increased survival over TMZ alone. Neither concurrent treatment with GTA and TMZ nor salvage therapy (GTA after a single course of TMZ) increased survival over TMZ alone.

The preliminary orthotopic results support a synergistic effect of GTA and TMZ (See Example 6). Based on the promotion of an open chromatin state by GTA acetylation of histones, experiments were performed in which subjects were "primed" with GTA 2 days prior to TMZ. Additional studies were performed to compare priming therapy with concurrent (GTA & TMZ started at day 5, then daily GTA) and salvage (daily GTA after TMZ ends) therapy (FIG. 8). Mice engrafted with OG35 GSCs and treated with GTA/TMZ concurrently or as salvage therapy survived no longer than those treated with TMZ alone. These data support the administration of GTA prior to TMZ is a cancer treatment regimen.

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed.

The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

What is claimed is:

1. A method for treating a cancer, the method comprising administering to a subject in need of treatment of a cancer, a glyceryltriacetate (GTA) compound in a therapeutically effective amount to treat the cancer, wherein the cancer is a glioma or a neuroblastoma.

2. The method of claim 1, wherein treating the cancer comprises decreasing cancer stem cell proliferation in the subject.

3. The method of claim 1, wherein treating the cancer comprises enhancing the cytosolic-nuclear shuttling of aspartoacylase (ASPA) and/or acetyl-CoA synthetase 1 (AceCS1).

4. The method of claim 1, wherein the GTA compound is administered to the subject orally, intragastrically, or is administered into a surgical incision, opening, or cavity in the subject.

5. The method of claim 1, further comprising administering one or more additional cancer-therapeutic agents to the subject.

6. The method of claim 5, wherein the one or more additional cancer-therapeutic agents is temozolomide, bevacizumab, bis-chloroethylnitrosourea (BCNU), Lomustine, procarbazine, or vincristine.

7. The method of claim 5, wherein the GTA compound and the one or more additional cancer chemotherapeutic agent are administered as a combination drug therapy.

8. The method of claim 1, further comprising administering to the subject a surgical treatment to remove or reduce the cancer in the subject.

9. The method of claim 1, wherein the GTA compound is administered to the subject in a pharmaceutical composition.

10. The method of claim 1, wherein the subject does not have Canavan disease.

11. The method of claim 1, wherein the subject is a human.

* * * * *